US012751924B2

(12) United States Patent
Li et al.

(10) Patent No.: US 12,751,924 B2

(45) Date of Patent: Oct. 6, 2026

(54) CAROTENOID PREPARATIONS, PREPARATION METHODS, AND APPLICATION THEREOF

(71) Applicant: INNOBIO CORPORATION LIMITED, Dalian (CN)

(72) Inventors: Qian Li, Dalian (CN); Chao Fan, Dalian (CN); Yongde Hong, Dalian (CN); Xiang Ren, Dalian (CN); Wenzhong Wu, Dalian (CN)

(73) Assignee: INNOBIO CORPORATION LIMITED, Dalian (CN)

(*) Notice: Subject to any disclaimer, the term of this patent is extended or adjusted under 35 U.S.C. 154(b) by 401 days.

(21) Appl. No.: 18/357,149

(22) Filed: Jul. 23, 2023

(65) Prior Publication Data

US 2024/0016741 A1 Jan. 18, 2024

Related U.S. Application Data

(63) Continuation of application No. PCT/CN2022/142679, filed on Dec. 28, 2022.

(30) Foreign Application Priority Data

Dec. 28, 2021 (CN) ......................... 202111633948.7
Dec. 28, 2021 (CN) ......................... 202111682238.3
Jan. 23, 2022 (CN) ......................... 202210083689.3

(51) Int. Cl.

| | |
|---|---|
| ***A61K 9/16*** | (2006.01) |
| ***A61K 31/01*** | (2006.01) |
| ***A61K 31/015*** | (2006.01) |
| ***A61K 31/047*** | (2006.01) |
| ***A61K 31/122*** | (2006.01) |
| ***A61K 36/28*** | (2006.01) |

(52) U.S. Cl.

CPC .......... *A61K 9/1652* (2013.01); *A61K 9/1623* (2013.01); *A61K 9/1694* (2013.01); *A61K 31/01* (2013.01); *A61K 31/015* (2013.01); *A61K 31/047* (2013.01); *A61K 31/122* (2013.01); *A61K 36/28* (2013.01); *A61K 2236/333* (2013.01); *A61K 2236/39* (2013.01); *A61K 2236/53* (2013.01)

(58) Field of Classification Search

CPC .. A61K 9/1652; A61K 9/1623; A61K 9/1694; A61K 31/01; A61K 31/015; A61K 31/047; A61K 31/122; A61K 36/28; A61K 2236/333; A61K 2236/39; A61K 2236/53; A61K 31/07; A23L 33/155; A23L 5/44; C07C 2601/16; C07C 403/24; A61P 27/02

See application file for complete search history.

(56) References Cited

U.S. PATENT DOCUMENTS

| | | | |
|---|---|---|---|
| 3,206,316 | A | 9/1965 | Kläui |
| 3,998,753 | A | 12/1976 | Antoshkiw et al. |
| 4,522,743 | A | 6/1985 | Horn et al. |
| 5,364,563 | A | 11/1994 | Cathrein et al. |
| 6,380,442 | B1 | 4/2002 | Madhavi et al. |
| 8,247,615 | B2 | 8/2012 | Reilly et al. |
| 2001/0008644 | A1 | 7/2001 | Stein et al. |
| 2005/0008746 | A1 | 1/2005 | Beck et al. |
| 2006/0051479 | A1 | 3/2006 | Chiavazza et al. |
| 2010/0267838 | A1 | 10/2010 | Köpsel |
| 2010/0272861 | A1 | 10/2010 | Lindemann et al. |
| 2012/0018912 | A1 | 1/2012 | Chen et al. |
| 2013/0171298 | A1 | 7/2013 | Deshpande |
| 2015/0201659 | A1 | 7/2015 | Zach et al. |
| 2016/0243240 | A1 | 8/2016 | Musaeus et al. |
| 2019/0090517 | A1 | 3/2019 | Beck et al. |
| 2019/0098924 | A1 | 4/2019 | Estrella et al. |
| 2020/0339498 | A1 | 10/2020 | Heining et al. |

FOREIGN PATENT DOCUMENTS

| | | | |
|---|---|---|---|
| CN | 1836652 | A | 9/2006 |
| CN | 101032683 | A * | 9/2007 |
| CN | 101219125 | A | 7/2008 |
| CN | 101260071 | A | 9/2008 |
| CN | 101292950 | A | 10/2008 |

(Continued)

OTHER PUBLICATIONS

Eggersdorfer M, Wyss A. Carotenoids in human nutrition and health. Arch Biochem Biophys. Aug. 15, 2018;652:18-26, 9 pages. doi: 10.1016/j.abb.2018.06.001. Epub Jun. 6, 2018. PMID: 29885291. (Year: 2018).*

(Continued)

*Primary Examiner* — Aaron J Kosar

*Assistant Examiner* — Jennifer Lynn Cain

(74) *Attorney, Agent, or Firm* — METIS IP LLC

(57) ABSTRACT

The disclosure provides a carotenoid preparation, its preparation method and application. The method includes: obtaining pretreated carotenoid by mixing carotenoid and ethanol aqueous solution, stirring, and then dispersing through high-speed shearing, adding antioxidant, and removing solvent until ethanol solution residue is less than 10 ppm, a moisture content of the pretreated carotenoid being within a range of 10%-30%; obtaining a pretreated gelling wall material by preparing an aqueous solution with a first solid content through mixing wall material and carbohydrate, stirring, and dispersing; and obtaining the carotenoid preparation by mixing the pretreated carotenoid and the pretreated gelling wall material, emulsifying, and granulating.

11 Claims, 11 Drawing Sheets

(56) References Cited

FOREIGN PATENT DOCUMENTS

| | | | | | |
|---|---|---|---|---|---|
| CN | 101292965 | A | | 10/2008 | |
| CN | 101439029 | A | | 5/2009 | |
| CN | 101168522 | B | | 12/2010 | |
| CN | 102389108 | A | | 3/2012 | |
| CN | 103284290 | A | | 9/2013 | |
| CN | 103406079 | A | | 11/2013 | |
| CN | 104511267 | A | | 4/2015 | |
| CN | 105166092 | A | | 12/2015 | |
| CN | 104146988 | B | | 6/2016 | |
| CN | 105747216 | A | | 7/2016 | |
| CN | 106316909 | A | | 1/2017 | |
| CN | 106748947 | A | | 5/2017 | |
| CN | 107048367 | A | | 8/2017 | |
| CN | 108185424 | A | * | 6/2018 | ............. A61K 31/07 |
| CN | 108578370 | A | | 9/2018 | |
| CN | 109157510 | A | | 1/2019 | |
| CN | 109198382 | A | | 1/2019 | |
| CN | 111248433 | A | | 6/2020 | |
| CN | 111328953 | A | | 6/2020 | |
| CN | 111419821 | A | | 7/2020 | |
| CN | 112056558 | A | | 12/2020 | |
| CN | 112075630 | A | | 12/2020 | |
| CN | 112494454 | A | | 3/2021 | |
| CN | 112535293 | A | | 3/2021 | |
| CN | 108185424 | B | | 8/2021 | |
| CN | 113952759 | A | | 1/2022 | |
| CN | 114276285 | A | | 4/2022 | |
| CN | 114287625 | A | | 4/2022 | |
| CN | 114504104 | A | | 5/2022 | |
| JP | H11322708 | A | | 11/1999 | |
| JP | 2007055953 | A | | 3/2007 | |
| JP | 2010130903 | A | | 6/2010 | |
| WO | 2006114794 | A1 | | 11/2006 | |
| WO | WO-2017168005 | A1 | * | 10/2017 | ........... A61K 9/2018 |

OTHER PUBLICATIONS

CN-101032683-A, Translation, 5 pages. (Year: 2007).*

CN-108185424-A, Translation, 9 pages. (Year: 2018).*

International Search Report in PCT/CN2022/142679 mailed on Mar. 18, 2023, 6 pages.

Written Opinion in PCT/CN2022/142679 mailed on Mar. 18, 2023, 6 pages.

Prabhjot Kaur et al., Encapsulation of Carotenoids with Sucrose by Co-Crystallization: Physicochemical Properties, Characterization and Thermal Stability of Pigments, LWT—Food Science and Technology, 140: 1-10, 2021.

Ma, Kongjun et al., Optimized Technology and Kinetic Characteristics of Saponification of Lutein Esters by Response Surface Methodology, Food Science and Technology, 40(10): 197-201, 2015.

Zheng, Jianxian, Key Technologies and Typical Examples of Plant Active Substances Production, Scientific and Technical Documents Publishing House, 2006, 30 pages.

* cited by examiner

Peak table
Detector A 453

| Peak number | Retention time | Area | Height | Area (%) | Mark | Name of compound |
|---|---|---|---|---|---|---|
| 1 | 9.102 | 101646 | 1198 | 0.810 | M | 3S, 3'S-zeaxanthin |
| 2 | 41.866 | 24183 | 470 | 0.193 | M | 3R, 3'S-meso- zeaxanthin |
| 3 | 44.814 | 10980013 | 130572 | 87.491 | M | 3R, 3'R-zeaxanthin |
| 4 | 47.128 | 814268 | 10809 | 6.488 | V M | Lutein |
| 5 | 52.107 | 462208 | 4790 | 3.683 | M | |
| 6 | 91.640 | 167582 | 3549 | 1.335 | M | |
| Total | | 12549901 | 151387 | 100.00 | | |

CAROTENOID PREPARATIONS, PREPARATION METHODS, AND APPLICATION THEREOF

CROSS-REFERENCE TO RELATED APPLICATIONS

This application is a Continuation of International Application No. PCT/CN2022/142679, filed on Dec. 28, 2022, which claims the priority of the Chinese Patent Application No. 202111633948.7, filed on Dec. 28, 2021, the Chinese Patent Application No. 202111682238.3, filed on Dec. 28, 2021, and the Chinese Patent Application No. 202210083689.3, filed on Jan. 23, 2022, the entire contents of which are incorporated herein by reference.

TECHNICAL FIELD

The present disclosure relates to the technical field of microparticle preparation, and in particular to carotenoid preparations, preparation methods, and application thereof.

BACKGROUND

As the main source of vitamin A in the human body, carotenoids have the functions of immune regulation, anti-oxidation, anti-cancer, anti-aging, etc., which can have beneficial effects on human health. However, carotenoids are insoluble in water, have low solubility in oil, and are unstable in light, oxygen, and heat environments, which limits the application of carotenoid-related preparations. In addition, for carotenoids such as lutein, lutein may be prepared by saponification, which requires a large amount of alkali and takes a long time for saponification, resulting in alkaline wastewater, which is not friendly to the environment.

Therefore, it is necessary to provide a carotenoid preparation, preparation methods, and application, so as to optimize the preparation process of carotenoid and improve the stability and application of the carotenoid preparation.

SUMMARY

One or more embodiments of the present disclosure provide a carotenoid preparation. The carotenoid preparation is obtained by mixing pretreated carotenoid with pretreated gelling wall material, emulsifying, and granulating. An amount of the pretreated gelling wall material is 40%-80% of a weight of the carotenoid preparation. Raw material of the pretreated gelling wall material includes wall material and carbohydrate. The wall material includes a mixture of modified starch or starch and cellulose derivative. The carbohydrate includes at least one of sucrose, glucose, glucose syrup, xylose, maltooligosaccharide, fructooligosaccharide, and solid corn syrup.

One or more embodiments of the present disclosure provide a method for preparing a carotenoid preparation. The method includes: obtaining pretreated carotenoid by mixing carotenoid and ethanol aqueous solution, stirring, and then dispersing through high-speed shearing, adding antioxidant, and removing solvent until ethanol solution residue is less than 10 ppm, a moisture content of the pretreated carotenoid being within a range of 10%-30%; obtaining a pretreated gelling wall material by preparing an aqueous solution with a first solid content through mixing wall material and carbohydrate, stirring, and dispersing; and obtaining the carotenoid preparation by mixing the pretreated carotenoid and the pretreated gelling wall material, emulsifying, and granulating.

One or more embodiments of the present disclosure provide an application of the carotenoid preparation. The application includes an application in the fields of food, drink, health care product, and medicine.

BRIEF DESCRIPTION OF THE DRAWINGS

The present disclosure is further described in terms of exemplary embodiments. These exemplary embodiments are described in detail with reference to the drawings. These embodiments are not limited, in these embodiments, the same number denote the same structure, wherein.

DETAILED DESCRIPTION

Figure 1:
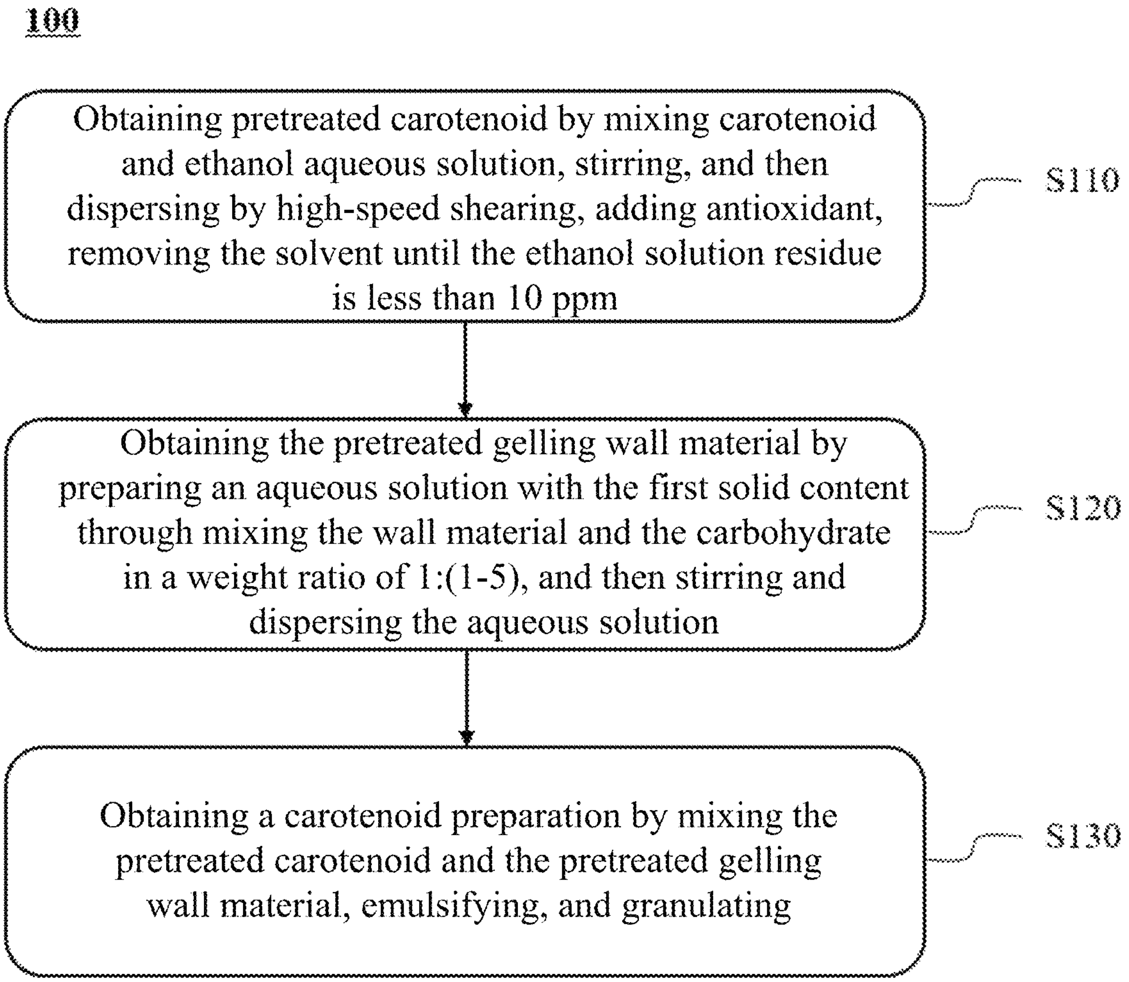
FIG. 1 is an exemplary flowchart illustrating a process of a method for preparing a carotenoid preparation according to some embodiments of the present disclosure.

In order to more clearly explain the technical scheme of the embodiment of this description, a brief description of the accompanying drawings required for the embodiment description is given below. Obviously, the accompanying drawings below are only some examples or embodiments of this description, and it is possible for ordinary technicians skilled in the art to apply this description to other similar scenarios according to these accompanying drawings without creative effort. Unless obviously obtained from the context or the context illustrates otherwise, the same numeral in the drawings refers to the same structure or operation.

It should be understood that the "system", "device", "unit" and/or "module" used in this disclosure are a method used to distinguish different components, elements, parts, portions or assemblies of different levels. However, the words may be replaced by other expressions if other words can achieve the same purpose.

As shown in this description and claims, the words "one", "a", "a kind" and/or "the" are not special singular but may include the plural unless the context expressly suggests otherwise. Generally speaking, the terms "comprise" and "include" only imply that the clearly identified steps and elements are included, and these steps and elements do not constitute an exclusive list, and the method or apparatus may also include other steps or elements.

Carotenoids are physiological antioxidants that can hinder lipid peroxidation and have beneficial effects on health. However, carotenoids are insoluble in water, have very low solubility in fats and oils. At the same time, carotenoids have low stability, which are unstable to light, oxygen, and heat. In the conventional methods, embedded products are formed by microencapsulation of carotenoids, which may improve their bioavailability, and also improve their coloring ability at the same time, resulting in easy staining of clothes, hands, etc. during the use of carotenoid products, which affects beauty and brings consumers a bad experience.

Carotenoids include lutein having antioxidant effects, which may protect eyesight and delay early arteriosclerosis. At present, the traditional process generally uses saponification of lutein esters to prepare lutein, but a large amount of alkali is used in this process, resulting in alkaline wastewater, and a large amount of organic solvents are used at the same time, which is not friendly to the environment, the saponification time is relatively long, and the purity of lutein in the prepared product is low.

Some embodiments of the disclosure provide carotenoid preparations, preparation methods, and application. In some embodiments, carotenoid may be pretreated, pretreated gelling wall material may be prepared using wall material of different materials and carbohydrate in different weight ratios, and carotenoid preparation may be prepared according to the pretreated carotenoid and pretreated gelling wall material, which can not only reduce the release rate of carotenoid in hydrochloric acid solution, avoid destruction by gastric acid, maintain the biological activity of carotenoid, but also effectively reduce the pigment dissolution rate, and avoid staining clothes, tongue, hands, etc. during the use of carotenoid products. In some embodiments, when preparing lutein crystal, lutein is prepared by tubular reaction combined with alcoholysis, and lutein is purified by complexing agent, which can shorten the production time, reduce the amount of alkali, be environmentally friendly, and improve the production efficiency of lutein crystals.

In some embodiments, the carotenoid preparation may be applied in various fields, such as food, drink, health product, medicine, or other fields. In some embodiments, carotenoid preparation may also be applied to prepare products, soft candy, solid drinks, liquid drinks, tablets, solid preparations, eye gel or eye drops that require nutrient visualization.

Carotenoids are physiological antioxidants that can hinder lipid peroxidation and have beneficial effects on health. However, carotenoids are insoluble in water, which have very low solubility in fats and oils. At the same time, carotenoids have low stability, which are unstable to light, oxygen, and heat. In conventional methods, the embedding products are formed by microencapsulating carotenoids, which can improve bioavailability and also improve dyeing ability, resulting in easy staining of clothes, hands, etc. during the use of carotenoid products. In some embodiments of the disclosure, carotenoid preparation is obtained by pretreating carotenoid and adding antioxidant, and using gelling wall material to embed the pretreated carotenoid, which can not only maintain the biological activity of carotenoid, but also effectively reduce the pigment dissolution rate.

In some embodiments, the carotenoid preparation may be obtained by mixing pretreated carotenoid and pretreated gelling wall material, emulsifying, and granulating. For more details about the preparation method of the carotenoid preparation, please refer to FIG. 1 and its related descriptions, which will not be repeated here.

In some embodiments, an amount of the pretreated gelling wall material may be within a range of 40%-80% of a weight of the carotenoid preparation. In some embodiments, the amount of the pretreated gelling wall material may be within a range of 60%-80% of the weight of the carotenoid preparation. In some embodiments, the amount of the pretreated gelling wall material may be within a range of 65%-70% of the weight of the carotenoid preparation.

In some embodiments, raw material of the pretreated gelling wall material may include wall material and carbohydrate. In some embodiments, a weight ratio of wall material to carbohydrate may be within a range of 1:(1-5). In some embodiments, the weight ratio of the wall material to carbohydrate may be within a range of 1:(2-4). In some embodiments, the weight ratio of the wall material to carbohydrate may be within a range of 1:(3-4). In some embodiments, the wall material may include a mixture of starch and cellulose derivative. The starch is a kind of natural macromolecular compound of polysaccharide substances polymerized from glucose molecules. For example, the starch may include, but is not limited to, corn starch, tapioca starch, potato starch, or the like. In some embodiments, the wall material may also include acacia senegal. In some embodiments, the carbohydrate may include at least one of sucrose, glucose, glucose syrup, xylose, maltooligosaccharide, fructooligosaccharide, and solid corn syrup.

In some embodiments, carotenoid may include at least one of lutein, lutein fatty acid ester, zeaxanthin, lycopene, α-carotene, β-carotene, canthaxanthin, and astaxanthin.

In some embodiments, a total pigment content of the pretreated carotenoid may be greater than 70%. In some embodiments, the total pigment content of the pretreated carotenoid may be greater than 80%. In some examples, the total pigment content of the pretreated carotenoid may be greater than 90%.

In some embodiments, the raw material of the pretreated carotenoid may be obtained by mixing lutein or lutein fatty acid ester, zeaxanthin, and β-carotene in the weight ratio of (1-3):(1-3):(1-3). In some embodiments, the raw material of pretreated carotenoid may be obtained by mixing lutein or lutein fatty acid ester, zeaxanthin, and β-carotene in the weight ratio of (2-3):(1-2):(1-2). In some embodiments, the raw material of the pretreated carotenoid may be obtained by mixing lutein or lutein fatty acid ester, zeaxanthin, and β-carotene in the weight ratio of (1-2):(1-2):(1-2).

In some embodiments, the pretreated zeaxanthin crystal may include two isomers of (3R, 3'R)-zeaxanthin and (3R, 3'S)-zeaxanthin, and the two isomers may account for more than 80% of weight of zeaxanthin crystal. In some embodiments, the weight ratio between the two isomers of (3R, 3'R)-zeaxanthin and (3R, 3'S)-zeaxanthin may be within a range of (5-15%):(95-85%).

In some embodiments, the wall material may be a mixture of starch and cellulose derivative in a weight ratio of 1:(1-2). In some embodiments, the wall material may be a mixture of starch and cellulose derivative in a weight ratio of 1:(1-1.8). In some embodiments, the wall material may be a mixture of starch and cellulose derivative in a weight ratio of 1:(1.2-1.5).

In some embodiments, the pigment dissolution rate of the carotenoid preparation in water may be less than 1%. In some embodiments, the pigment dissolution rate of the carotenoid preparation in water may be less than 0.5%. In some embodiments, the pigment dissolution rate of the carotenoid preparation in water may be less than 0.3%.

FIG. 1 is an exemplary flowchart illustrating a process of a method for preparing a carotenoid preparation according to some embodiments of the present disclosure. Process 100 may include the following steps.

Step S110: obtaining pretreated carotenoid by mixing carotenoid and ethanol aqueous solution, stirring, and then dispersing by high-speed shearing, adding antioxidant, removing the solvent until the ethanol solution residue is less than 10 ppm.

In some embodiments, the moisture content of the pretreated carotenoid may be within a range of 10%-30%. In some embodiments, the moisture content of the pretreated carotenoid may be within a range of 10%-25%. In some embodiments, the moisture content of the pretreated carotenoid may be within a range of 20%-30%.

In some embodiments, the raw material of the carotenoid may be obtained by mixing lutein or lutein fatty acid ester, zeaxanthin, and β-carotene in the weight ratio of (1-3):(1-3):(1-3). For more details about the raw material of carotenoid, please refer to the foregoing description, which will not be repeated here.

In some embodiments, carotenoid may be mixed with 3-5 times of ethanol aqueous solution. In some embodiments, carotenoid may be mixed with 3-3.8 times of ethanol aqueous solution. In some embodiments, carotenoid may be mixed with 4-5 times of ethanol aqueous solution.

In some embodiments, a mass fraction of the ethanol aqueous solution may be within a rang of 50%-70%. In some embodiments, the mass fraction of the ethanol aqueous solution may be within a range of 50%-60%. In some embodiments, the mass fraction of the ethanol aqueous solution may be within a range of 55%-70%.

In some embodiments, the mixed solution may be stirred for at least 20 min at a temperature of 40° C.-50° C. and then dispersed by high-speed shearing. In some embodiments, the mixed solution may be stirred for at least 20 min at 40° C.-45° C. and then dispersed by high-speed shearing.

In some embodiments, the pretreated carotenoid may be obtained by adding an antioxidant to the mixed solution and removing the solvent at a temperature of 70° C.-80° C. until the ethanol solution residue is less than 10 ppm.

In some embodiments, the amount of the added antioxidant may be within a range of 5%-30% of the weight of the carotenoid. In some embodiments, the amount of the added antioxidant may be within a range of 5%-20% of the weight of the carotenoid. In some embodiments, the amount of the added antioxidant may be within a range of 15%-30% of the weight of the carotenoid.

In some embodiments, antioxidant may include at least one of ascorbic acid, ascorbyl palmitate, sucrose fatty acid ester, tocopherol, fatty acid ascorbate, butylated hydroxytoluene, butylated hydroxyanisole, propyl gallic acid, and tert butyl hydroxyquinone. In some embodiments, the antioxidant may be a mixture of ascorbic acid, ascorbyl palmitate, and sucrose fatty acid ester.

In some embodiments, the weight ratio of ascorbic acid, ascorbyl palmitate, and sucrose fatty acid ester may be within a range of (2-5):(0.1-3):(0.1-3). In some embodiments, the weight ratio of ascorbic acid, ascorbyl palmitate, and sucrose fatty acid ester may be within a range of (2-4):(0.1-2):(0.1-2). In some embodiments, the weight ratio of ascorbic acid, ascorbyl palmitate, and sucrose fatty acid ester may be within a range of (2-4):(2-3):(2-3).

Step S120: obtaining the pretreated gelling wall material by preparing an aqueous solution with the first solid content through mixing the wall material and the carbohydrate in a weight ratio of 1:(1-5), and then stirring and dispersing the aqueous solution.

In some embodiments, the wall material and the carbohydrate may also be mixed in a weight ratio of 1:(1-4). In some embodiments, the wall material and the carbohydrate may be mixed in a weight ratio of 1:(3-5).

In some embodiments, the aqueous solution with a first solid content may be an aqueous solution with a solid content of 50%-70%. In some embodiments, the aqueous solution with a first solid content may be an aqueous solution with a solid content of 50%-60%. In some embodiments, the aqueous solution with a first solid content may be an aqueous solution with a solid content of 55%-70%.

In some embodiments, the aqueous solution may be stirred and dispersed at 50° C.-70° C., and then stirred at 80° C.-90° C. for 15 min-45 min.

In some embodiments, the wall material may be a mixture of starch and cellulose derivative. In some embodiments, starch and cellulose derivative may be mixed in a weight ratio of 1:(1-2). In some embodiments, starch and cellulose derivative may be mixed in a weight ratio of 1:(1.2-1.5).

In some embodiments, the cellulose derivative may include at least one of hypromellose, methylcellulose, ethylcellulose, and sodium carboxymethylcellulose. In some embodiments, a viscosity of the cellulose derivative may be within a range of 2 cP-15 cP. In some embodiments, the viscosity of the cellulose derivative may be within a range of 5 cP-12 cP. In some embodiments, the viscosity of the cellulose derivative may be within a range of 7 cP-10 cP.

Step S130: obtaining a carotenoid preparation by mixing the pretreated carotenoid and the pretreated gelling wall material, emulsifying, and granulating.

According to the above process, the carotenoid preparation is prepared through pretreating carotenoid, adding antioxidant, and embedding the pretreated carotenoid with gelling wall material, which can effectively reduce the pigment dissolution rate of the product, improve the stability of the carotenoid, and maintain biological activity. In addition, no organic solvent is used in the preparation process, making the whole preparation process more environmentally friendly.

The preparation method of the carotenoid preparation is described in detail below through embodiments A1-A4, comparative embodiments A5-A7, and effect embodiments A8-A9. It should be noted that the reaction conditions, reaction materials, and the amount of reaction materials in embodiments A1-A4 are only for illustrating the preparation method of carotenoid preparation, and do not limit the protection scope of this disclosure. Embodiments A1-A4 are embodiments using different reaction conditions and material weight ratios respectively. Comparative embodiments A5-A7 are control groups for embodiments A2-A4. Effect embodiments A8-A9 are comparisons of the actual effects of the product prepared according to embodiment A2 and the product prepared according to the prior art.

In the disclosure, unless otherwise explicitly stated, percentages and contents are calculated by mass. Unless otherwise specified, the used experimental methods are conventional methods, and the used materials and reagents may be purchased from commercial source.

In the preparation process of the carotenoid preparation in the disclosure, one or more of the following components may also be selectively added according to the conventional dosage in this field:

(1) Water-soluble ingredient. The water-soluble ingredient may include, but not limited to, one or more of glucose, lactose, maltooligosaccharide, polyethylene glycol, sodium carboxymethylcellulose, and solid glucose syrup.

(2) Surfactant. The surfactant may be used to solve the problem that products made of water-insoluble fat or waxy material usually float on the water surface, and increase the water dispersibility of the product. The surfactant may include but not limited to one or more of Tween 60, Tween 80, or sucrose fatty acid ester.

(3) Binder. The binder may include but not limited to one or more of povidone, glycerin, propylene glycol, polyglycerol fatty acid ester, soluble soybean polysaccharide, and sodium carboxymethylcellulose.

(4) Suspending agent. The suspending agent may include but not limited to one or more of guar gum, xanthan gum, sodium alginate, hydroxypropyl methylcellulose, methylcellulose, gellan gum, and carrageenan.

(5) Diluent. The diluent may include but not limited to one or more of starch, maltodextrin, and calcium hydrogen phosphate.

(6) Stabilizer. The stabilizer may include but not limited to one or more of sodium lactate, sodium citrate, magnesium carbonate, sodium bicarbonate, and microcrystalline cellulose.

(7) Glidant. The glidant may include but not limited to one or more of silicon dioxide, corn starch, and calcium silicate.

(8) Antioxidant. The antioxidant may include but not limited to one or more of vitamin E, vitamin C, vitamin E derivative, and vitamin C derivative.

(9) Acidity regulator. The acidity regulator may include but not limited to one or more of citric acid, lactic acid, and malic acid.

In this disclosure, the following methods are used to measure and evaluate the product.

The method for measuring the pigment dissolution rate described in this disclosure is: taking 1 g the product and adding 50 mL water, stirring and dissolving for 30 min under the temperature of 90° C. and the rotation speed of 100 rpm, then filtering and transferring the filtrate to a volumetric flask, washing the filtrate once using 30 mL water, combining the filtrate, and measuring the optical density (OD) at the maximum absorption wavelength after constant volume. The pigment dissolution rate is (OD/mass of the product)×100%.

The evaluation method of accelerated stability of the product in this disclosure is the method provided by the Chinese Pharmacopoeia: under the condition of temperature of 40° C. and 75% of relative humidity (RH), measuring the pigment content at different times to determine stability, and using pigment retention rate to indicate stability of product. Pigment retention rate is a ratio of product content to initial content at different time, which may be expressed as a percentage.

Embodiment A1: Effect of Processing Method of the Crystal on Stability of the Crystal (1) The zeaxanthin crystal A may be obtained by mixing 160 g zeaxanthin crystal with 4 times of 60% ethanol aqueous solution, stirring at 45° C. for 30 min, then dispersing by high-speed shearing at 10,000 rpm, adding 28 g ascorbic acid, 10 g ascorbyl palmitate, and 10 g sucrose fatty acid ester, and removing the solvent at 75° C. The ethanol soluble residue in zeaxanthin crystal A is 8 ppm, and the moisture content of the zeaxanthin crystal is 12.3%.

(2) The zeaxanthin crystal B may be obtained by mixing 160 g zeaxanthin crystal with 4 times of 60% ethanol aqueous solution, stirring at 45° C. for 30 min, then dispersing through high-speed shearing at 10,000 rpm, adding 28 g ascorbic acid and 10 g ascorbyl palmitate, and removing the solvent at 75° C. The ethanol soluble residue in zeaxanthin crystal B is 55 ppm, and the moisture content of the zeaxanthin crystal is 25%.

(3) The zeaxanthin crystal C may be obtained by mixing 160 g zeaxanthin crystal with 8 times of 80% ethanol aqueous solution, stirring at 45° C. for 30 min, then dispersing by high-speed shearing at 10,000 rpm, adding 28 g of ascorbic acid, 10 g of ascorbyl palmitate, and 10 g sucrose fatty acid ester, removing the solvent at 75° C. The ethanol soluble residue in zeaxanthin crystal C is 155 ppm, and the moisture content of the zeaxanthin crystal is 32%.

(4) The zeaxanthin crystal D may be obtained by mixing 160 g zeaxanthin crystal, 28 g ascorbic acid, 10 g ascorbyl palmitate, and 10 g sucrose fatty acid ester.

(5) The pigment retention rate at different times may be measured by heating the above-mentioned zeaxanthin crystals A-D at 60° C., the measurement results are shown in Table 1.

TABLE 1

| | Pigment retention rate at different times | | | |
|---|---|---|---|---|
| | A | B | C | D |
| 0 | 100% | 100% | 100% | 100% |
| 1 h | 95.4% | 88.2% | 60.1% | 55.2% |
| 2 h | 93.1% | 65.2% | 55.0% | 40.4% |
| 3 h | 90.2% | 55.0% | 35.0% | 28.1% |

Through the comparison of pigment retention rate of zeaxanthin crystals A-D, it can be seen that compared with zeaxanthin crystal B with ethanol soluble residue greater than 10 ppm after removing solvent, zeaxanthin crystal C obtained by mixing carotenoid with more than 5 times of ethanol aqueous solution, and zeaxanthin crystal D obtained without pretreatment, the pigment retention rate of zeaxanthin crystal A is significant greater, and the zeaxanthin crystal A with the moisture content of 12.3% (within the range of 10%-30%) is obtained by mixing carotenoid with 4 times (within the range of 3-5 times) of ethanol water solution, stirring, high-speed shear dispersion, adding antioxidant, and removing solvent until the ethanol soluble residue is 8 ppm (less than 10 ppm).

In some embodiments, zeaxanthin crystal including different isomer ratios are also selected to conduct comparative experiments according to embodiment A1, that is, zeaxanthin crystal contains the two isomers of zeaxanthin (3R, 3'R)-zeaxanthin and (3R, 3'S)-zeaxanthin, the two isomers account for more than 80% of the weight of zeaxanthin crystal. In some embodiments, the weight ratio between the two isomers (3R, 3'R)-zeaxanthin and (3R, 3'S)-zeaxanthin may be within a range of (5%-15%):(95%-85%), which does not affect the result of the pigment retention rate of the zeaxanthin crystal A prepared according to the step (1) of embodiment A1.

Embodiment A2

The treated lutein crystal may be obtained by mixing 178 g lutein crystal with 3 times of 60% ethanol aqueous solution, stirring at 45° C. for 30 min, and then dispersing through high-speed shearing at 10,000 rpm, adding 20 g ascorbic acid, 1 g ascorbyl palmitate, and 1 g sucrose fatty acid ester, and removing the solvent at 75° C., and the treated lutein crystal is frozen at −20° C. for standby. The ethanol soluble residue of the treated lutein crystal is 7 ppm, and the moisture content of lutein crystal is 10%. An aqueous solution with a solid content of 50% is obtained by mixing 160 g cornstarch, 480 g sucrose, and 160 g hydroxypropyl methylcellulose (viscosity of 15 cP), and the aqueous solution is heated up to 90° C., stirred at a constant speed for 45 min, and placed at room temperature after stirring and dispersing at 60° C. The gelling wall material and the treated lutein crystal are mixed, stirred, emulsified, and spray-dried. The lutein product A is obtained, the pigment dissolution rate of which is 0.2%.

Embodiment A3

The treated β-carotene crystal is obtained by mixing 212 g β-carotene crystal with 5 times of 50% ethanol aqueous solution, stirring at 40° C. for 40 min, and then dispersing through high-speed shearing at 10,000 rpm, adding 17 g ascorbic acid, 25.5 g ascorbyl palmitate, and g sucrose fatty acid ester, and removing the solvent at 70° C., and the treated β-carotene crystal is frozen at −20° C. for standby. The ethanol soluble residue of the treated β-carotene crystal is 5 ppm, and the moisture content of the β-carotene crystal is 15%. An aqueous solution with a solid content of 50% is obtained by mixing 160 g tapioca starch, 480 g sucrose, and 160 g hydroxypropyl methylcellulose (viscosity of 2.5 cP), and the aqueous solution is heated up to 80° C., stirred at a constant speed for 15 min, and placed at room temperature after stirring and dispersing at 50° C. The gelling wall material and the treated β-carotene crystal are mixed, stirred, emulsified, and spray-dried. The β-carotene crystal product A is obtained, the pigment dissolution rate of which is 0.4%.

Embodiment A4

The treated composite crystal is obtained by mixing 81 g β-carotene crystal, 162 g lutein ester crystal, 81 g zeaxanthin crystal, and 4 times of 70% ethanol aqueous solution, stirring at 50° C. for 55 min, and then dispersing through high-speed shear at 10,000 rpm, adding 73 g ascorbic acid, 1.5 g ascorbyl palmitate, and 1.5 g sucrose fatty acid ester, and removing solvent at 80° C., and the treated composite crystal is frozen at −20° C. for standby. The ethanol soluble residue in the treated composite crystal is 3 ppm, and the moisture content of the composite crystal is 30%. An aqueous solution with a solid content of 50% is prepared using 100 g potato starch, 300 g sucrose, and 200 g hydroxypropyl methylcellulose (viscosity of 5 cP), and the aqueous solution is heated up to 82° C., stirred at a constant speed for 30 min, and placed at room temperature after stirring and dispersing at 70° C. The gelling wall material and the treated composite crystal are mixed, stifled, emulsified, and spray-dried. The product A with a ratio of lutein ester, zeaxanthin, and β-carotene of 2:1:1 is obtained, the pigment dissolution rate of which is 0.26%.

It can be seen from embodiments A2-A4 that by mixing carotenoid with 3-5 times of 50%-70% ethanol aqueous solution, stirring, high-speed shear dispersion, adding antioxidant, and removing solvent, carotenoid crystal with ethanol soluble residue less than 10 ppm and moisture content of 10%-30% is obtained. At least starch and cellulose derivative are used as wall material, and the wall material and carbohydrate are mixed in a weight ratio of 1:(1-5), and then made into an aqueous solution with a solid content of 50-70%, and the pretreated gelling wall material is obtained by stirring and dispersing the aqueous solution; and the carotenoid preparation is prepared by mixing the treated carotenoid crystal with the gelling wall material. The pigment dissolution rate of the carotenoid preparation is less than 1%, which is not easy to cause staining of clothes, tongue, etc. during use of the carotenoid preparation.

Comparative Embodiment A5

The treated zeaxanthin crystal is obtained by mixing 178 g zeaxanthin crystal with 3 times of 60% ethanol aqueous solution, stirring at 45° C. for 30 min, and then dispersing through high-speed shearing at 10,000 rpm, adding 20 g ascorbic acid, 1 g ascorbyl palmitate, and 1 g sucrose fatty acid ester, and removing the solvent at 75° C., and the treated zeaxanthin crystal is frozen at −20° C. for standby. The ethanol soluble residue in the treated zeaxanthin crystal is 7 ppm, and the moisture content of the treated zeaxanthin crystal is 12.8%. An aqueous solution with 50% of solid content is prepared using 160 g tapioca starch, 480 g sucrose, and 160 g hydroxypropyl methylcellulose (viscosity of 10 cP), the treated zeaxanthin crystal is added into the aqueous solution, the zeaxanthin product B is obtained after stirring, emulsifying, and spray drying, and pigment dissolution rate of the zeaxanthin product B is 67.7%.

Compared with embodiments A2-A4, it can be seen that the wall material of comparative embodiment A5 is not undergone gelling treatment (without heating, stirring, and static treatment to make the wall material gelling), so the pigment dissolution rate of the prepared product increases, resulting in poor use effect.

Comparative Embodiment A6

200 g lutein crystal, 20 g ascorbic acid, 1 g ascorbyl palmitate, and 1 g sucrose fatty acid ester are mixed. An aqueous solution with a solid content of 50% is prepared using 160 g tapioca starch, 480 g sucrose, and 160 g hydroxypropyl methylcellulose (viscosity of 10 cP), and the aqueous solution is heated up to 80° C., stirred at a constant speed for 15 min, and placed at room temperature after stirring and dispersing at 50° C. The lutein product B is obtained by mixing gelling wall material and lutein crystal, stirring, emulsifying, and spray-drying, the pigment dissolution rate of which is 30.2%.

Compared with embodiments A2-A4, it can be seen that the lutein crystal in comparative embodiment A6 is not pretreated (the lutein crystal is not mixed and stirred with ethanol solution, and pretreated by high-speed shear dispersion and solvent removal), so the pigment dissolution rate of the prepared product increases, resulting in poor use effect.

Comparative Embodiment A7

The treated lutein ester crystal is obtained by mixing 200 g lutein ester crystal with 3 times of 60% ethanol aqueous solution, stirring at 45° C. for 30 min, and then dispersing through high-speed shearing at 10,000 rpm, adding 20 g ascorbic acid, 1 g ascorbyl palmitate, and 1 g sucrose fatty acid ester, and removing the solvent at 75° C., and the treated lutein ester crystal is frozen at −20° C. for standby. The ethanol soluble residue in the treated lutein ester crystal is 7 ppm, and the moisture content of the treated lutein ester crystal is 10%. The treated lutein ester crystal is respectively added to the gelling wall material composition in Table 2, and treated according to the gelling method in embodiment A2, the product effect is shown in Table 2 below.

TABLE 2

Comparison of dissolution effects using different gelling wall material

| Product | Composition of gel wall material | | Pigment dissolution |
|---|---|---|---|
| | Wall material | Carbohydrate | rate |
| Lutein ester product A | 195 g corn starch | 583 g sucrose | 81.5% |
| Lutein ester product B | 195 g hydroxypropyl methylcellulose (15 cP) | 583 g sucrose | 89.0% |
| Lutein ester product C | 195 g corn starch 583 g hydroxypropyl methylcellulose (15 cP) | / | 88.5% |
| Lutein ester product D | 195 g corn starch 390 g acacia senegal | 193 g sucrose | 31.0% |
| Lutein ester product E | 195 g corn starch 195 g hydroxypropyl methylcellulose (50 cP) | 388 g sucrose | 15.5% |

Compared with embodiments A2-A4, it can be seen that for the lutein ester product A and the lutein ester product B in comparative embodiment A7, only one wall material (corn starch or hydroxypropylmethyl cellulose) and carbohydrate (sucrose) are combined, the pigment dissolution rates of the lutein ester product A and the lutein ester product B increase, resulting in poor use effect. The preparation formula of the lutein ester product C in comparative embodiment A7 has no carbohydrate, and the pigment dissolution rate of the lutein ester product C increases, resulting in poor use effect. The lutein ester product D in comparative embodiment A7 uses corn starch and acacia senegal as wall material, and gelatinizes with sucrose, but the weight ratio of wall material to carbohydrate is not within the range of 1:(1-5), the pigment dissolution rate of the lutein ester product D increases, resulting in poor use effect. The lutein ester product E in comparative embodiment A7 uses high-viscosity hydroxypropyl methylcellulose as the wall material, and the pigment dissolution rate of the lutein ester product E increases, resulting in poor use effect. The products of embodiments A2-A4 are prepared by the preparation method of this disclosure, the pigment dissolution rates of the products are lower than that of each product in comparative embodiment A7, and the use effect is better.

Effect Embodiment A8

The composite product 1 is obtained using lutein prepared according to the method of patent CN108185424B (Patent Application No. CN201711456450.1), zeaxanthin, and (3-carotene in a weight ratio of 1:1:1. The composite product 2 is obtained using lutein prepared according to the method of embodiment A2, zeaxanthin, and β-carotene in a weight ratio of 1:1:1. The comparison parameters of the two products are shown in Table 3 below.

TABLE 3

Comparison parameters of two products

| Product | Bulk density | retention rate for accelerating 6 months at 40° C. | Pigment dissolution rate |
|---|---|---|---|
| Composite product 1 | 0.68 | 98.7% | 68.2% |
| Composite product 2 | 0.66 | 98.9% | 0.32% |

Through the comparison of composite product 1 and composite product 2, it can be seen that the pigment dissolution rate of composite product 2 prepared through the preparation process of this disclosure (embodiment A2) is lower than that of composite product 1 prepared according to the preparation method of the patent CN108185424B, indicating that compared with composite product 1, composite product 2 is not easy to cause staining of hands, tongue, and other parts, and has better application value, so the effect of composite product 2 prepared by using embodiment A2 is better.

Effect Embodiment A9: Application Evaluation of Soft Candy

The solution I is obtained by weighing 8 g gelatin, 44 g white sugar, and 55 g glucose syrup, adding water with 20% of solid content, stirring and dissolving, boiling the sugar at 120° C. until the solid content is about 85%, and adjusting pH=3-4.

Figure 2A:
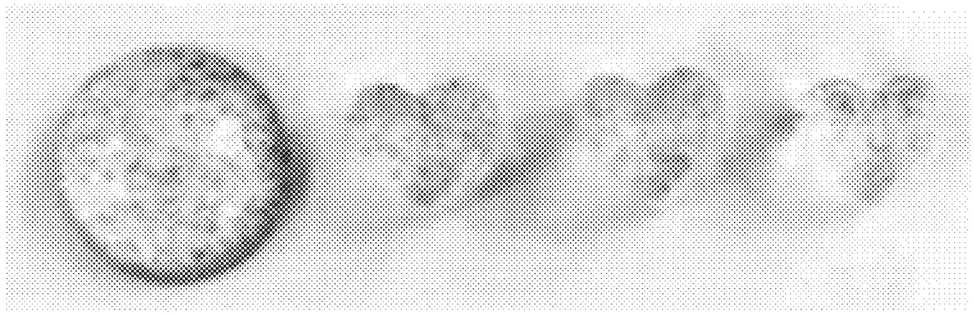
FIG. 2A is an exemplary appearance diagram of a soft candy of lutein product A according to some embodiments of the present disclosure.
Figure 2B:
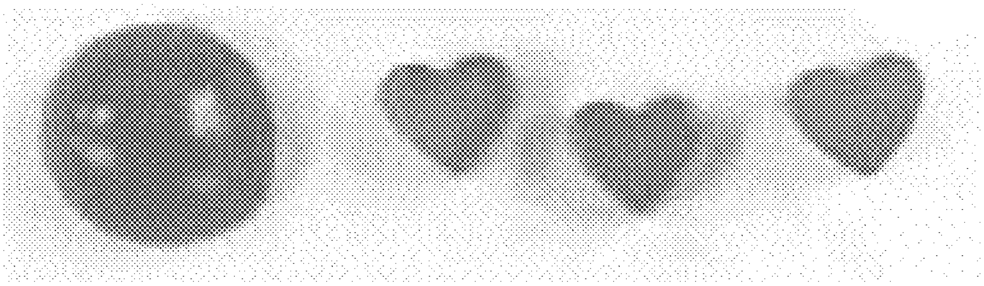
FIG. 2B is an exemplary appearance diagram of a soft candy of zeaxanthin product B according to some embodiments of the present disclosure.

20 g lutein product A prepared according to the method of embodiment A2 or 20 g zeaxanthin product B prepared according to the method of comparative embodiment A5 are added into the solution I, and the solution is stirred evenly and kept at 90° C. for 40 min. After injection molding and drying, the soft candy of lutein product A and the soft candy of zeaxanthin product B are obtained, the appearances of which are shown in FIG. 2A and FIG. 2B respectively. It can be seen that the lutein product A has no staining phenomenon in the soft candy, and is completely preserved in the soft candy, realizing the effect of nutritional visualization. However, zeaxanthin product B dyes the soft candy red, and the transparency of the soft candy decreases.

The above is only a preferred embodiment of the present disclosure, but the scope of protection of the present disclosure is not limited thereto. Changes or replacements that can easily be thought of by those skilled in the art within the scope of the disclosure should be included in the scope of protection of the disclosure. Therefore, the protection scope of the present disclosure should be determined by the protection scope of the claims.

In some embodiments, the carotenoid preparation may also be prepared by mixing pretreated carotenoid with pretreated gelling wall material with different components or different component ratios. For more details about the preparation method of the carotenoid preparation, please refer to FIG. 3 and its related descriptions, which will not be repeated here. In some embodiments of this disclosure, carotenoid are pretreated, starch is used as the raw material of the wall material, the pretreated gelling wall material is prepared using the wall material and carbohydrate in a weight ratio of (1-5):1, and the carotenoid preparation is prepared according to the pretreated carotenoid and gelling wall material, which not only can reduce the release rate of carotenoid in hydrochloric acid solution, avoid destruction by gastric acid, maintain the biological activity of carotenoid, at the same time, but also has a relatively large release rate in phosphate buffer, which is conducive to intestinal absorption. In addition, the carotenoid preparation may also effectively reduce the pigment dissolution rate and avoid staining clothes, tongues, hands, etc. during the use of carotenoid product.

In some embodiments, the raw material of pretreated carotenoid may be obtained by mixing lutein or lutein fatty acid ester, zeaxanthin, and β-carotene in the weight ratio (1-3):(1-3):(1-3). In some embodiments, the raw material of pretreated carotenoid may be obtained by mixing lutein or lutein fatty acid ester, zeaxanthin, and β-carotene in the weight ratio (2-3):(1-2):(1-2). In some embodiments, the raw material of pretreated carotenoid may be obtained by mixing lutein or lutein fatty acid ester, zeaxanthin, and β-carotene in the weight ratio (1-2):(1-2):(1-2).

In some embodiments, the pretreated zeaxanthin crystal includes two isomers of (3R, 3'R)-zeaxanthin and (3R, 3'S)-zeaxanthin, and the two isomers account for more than 80% of the weight of zeaxanthin crystal. In some embodiments, the weight ratio between the two isomers of (3R, 3'R)-zeaxanthin and (3R, 3'S)-zeaxanthin may be within a range of (5-15%):(95-85%).

In some embodiments, the amount of the pretreated gelling wall material may be within a range of 40%-70% of the weight of the carotenoid preparation. In some embodiments, the amount of the pretreated gelling wall material may be within a range of 45%-60% of the weight of the carotenoid preparation. In some embodiments, the amount of the pretreated gelling wall material may be within a range of 50%-70% of the weight of the carotenoid preparation.

In some embodiments, the raw material of the pretreated gelling wall material may include wall material and carbohydrate. In some embodiments, the weight ratio of wall material to carbohydrate may be within a range of (1-5):1. In some embodiments, the weight ratio of wall material to carbohydrate may be within a range of (2-4):1. In some embodiments, the weight ratio of wall material to carbohydrate may be within a range of (3-3.5):1. In some embodiments, the wall material may include modified starch. Modified starch refers to the polymer compound obtained by introducing new functional groups into starch molecule or changing the size of starch molecule and the property of starch granule using physical method, chemical method, or enzymatic method on the basis of starch. In some embodiments, modified starch may include, but is not limited to, starch sodium octenylsuccinate. In some embodiments, the wall material may also include acacia senegal. In some embodiments, the wall material may also include cellulose derivative.

For more details about the components that carbohydrate may include, the components that carotenoid may include, and the total content of pigment in pretreated carotenoid, please refer to the relevant description above.

In some embodiments, the pigment dissolution rate of the carotenoid preparation in water may be less than 5%. In some embodiments, the pigment dissolution rate of the carotenoid preparation in water may be less than 4%. In some embodiments, the pigment dissolution rate of the carotenoid preparation in water may be less than 3%.

In some embodiments, the release rate of the carotenoid preparation in gastrointestinal fluid for 0.5 h is less than 35%. In some embodiments, the release rate of the carotenoid preparation in gastrointestinal fluid for 0.5 h is less than 30%. In some embodiments, the release rate of the carotenoid preparation in gastrointestinal fluid for 0.5 h is less than 25%.

In some embodiments, the release rate of the carotenoid preparation in gastrointestinal fluid for 4 h is greater than 90%. In some embodiments, the release rate of the carotenoid preparation in gastrointestinal fluid for 4 h is greater than 95%. In some embodiments, the release rate of the carotenoid preparation in gastrointestinal fluid for 4 h is greater than 98%.

Figure 3:
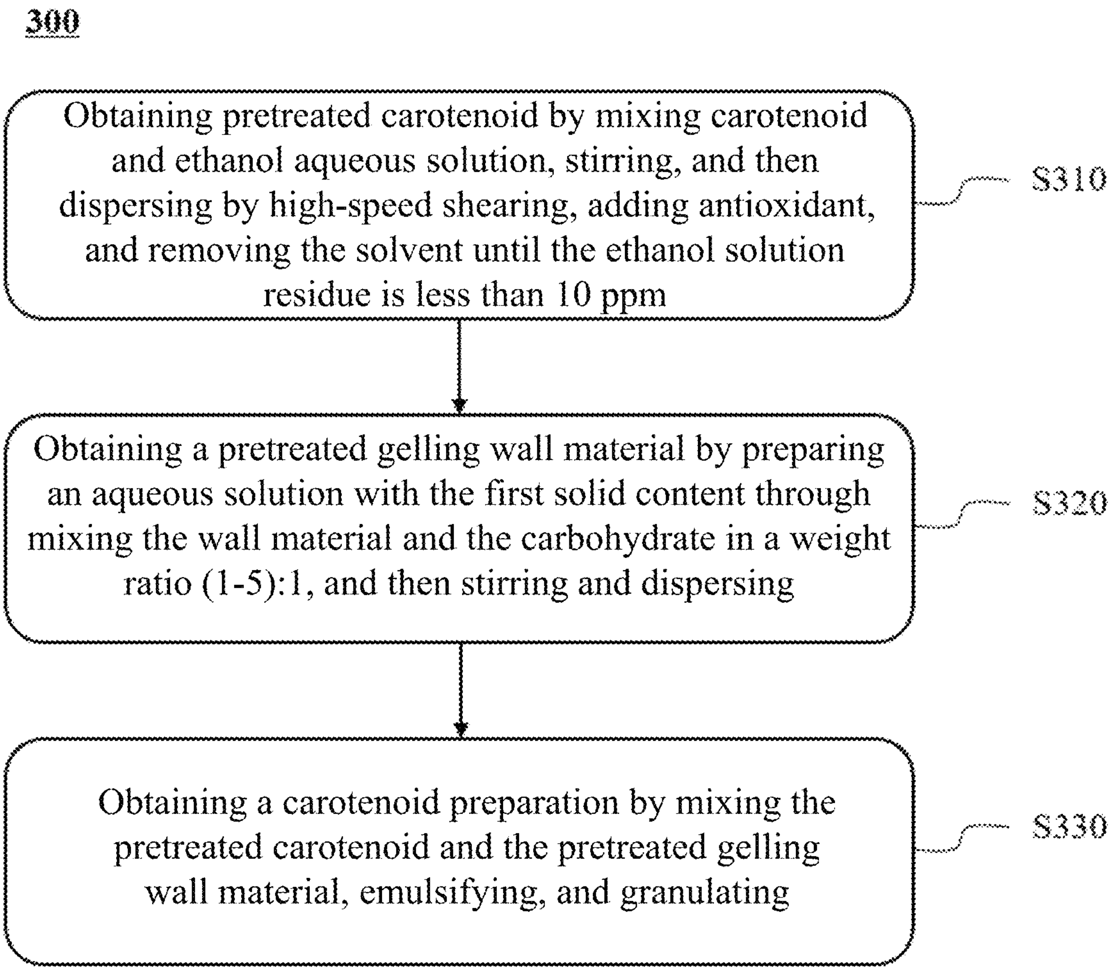
FIG. 3 is an exemplary flowchart illustrating a process of a method for preparing a carotenoid preparation according to some embodiments of the present disclosure.

FIG. 3 is an exemplary flowchart illustrating a process of a method for preparing a carotenoid preparation according to some other embodiments of the present disclosure. Process 300 may include the following steps.

Step S310: obtaining pretreated carotenoid by mixing carotenoid and ethanol aqueous solution, stirring, and then dispersing by high-speed shearing, adding antioxidant, and removing the solvent until the ethanol solution residue is less than 10 ppm.

For more details about step S310, refer to the relevant description of the above step S110.

In step S320, obtaining a pretreated gelling wall material by preparing an aqueous solution with the first solid content through mixing the wall material and the carbohydrate in a weight ratio (1-5):1, and then stirring and dispersing.

In some embodiments, the wall material and the carbohydrate may also be mixed in a weight ratio of (1-3):1. In some embodiments, the wall material and the carbohydrate may also be mixed in a weight ratio of (4-5):1.

For more details about the aqueous solution with the first solid content, please refer to the relevant description of FIG. 1, which will not be repeated here.

In some embodiments, the aqueous solution may be stirred and dispersed at 50° C.-70° C., then stirred at 80° C.-90° C. for 15 min-45 min, and cooled to 60° C.-65° C. for 100 min-150 min.

In some embodiments, the wall material may include sodium starch octenyl succinate. In some embodiments, carbohydrate may include glucose or glucose syrup and combinations thereof.

Step S330, obtaining a carotenoid preparation by mixing the pretreated carotenoid and the pretreated gelling wall material, emulsifying, and granulating.

The preparation method of the carotenoid preparation may be described in detail below through embodiments B1-B4, comparative embodiments B5-B8, and effect embodiments B9-B13. It should be noted that the reaction conditions, reaction material, and the amount of reaction material in embodiments B1-B4 are only for illustrating the preparation method of carotenoid preparation, and do not limit the protection scope of this description. The embodiments B1-B4 are embodiments using different reaction conditions and weight ratios of material respectively. Comparative embodiments B5-B8 are control groups for embodiments B2-B4. Effect embodiments B9-B13 are the comparison of the actual effect of the product prepared according to embodiment B2 and other products.

In this disclosure, unless otherwise explicitly stated, percentages and content are calculated by mass. Unless otherwise specified, the used experimental methods are conventional methods, and the materials and the used reagents may be purchased from commercial source.

In the preparation process of the carotenoid preparation in this disclosure, one or more of some components may also be added selectively according to the conventional dosage in this field. For more details about the selective addition of one or more of some components, please refer to the description, which will not be repeated here.

In this disclosure, the following methods are used to measure and evaluate the product.

For more details about the method for measuring the pigment dissolution rate in this disclosure, please refer to the foregoing description, which will not be repeated here.

For more details about the evaluation method of the accelerated stability of product of the present disclosure, please refer to the foregoing description, which will not be repeated here.

For the determination of the release rate in the disclosure, referring to USP<711> DISSOLUTION, the Apparatus 2 is used, the rotational speed is 50 rpm, and the release rate experiment is conducted according to the DELAYED-RELEASE DOSAGE FORMS method B. 0.1 N hydrochloric acid solution is selected as the release medium within 2 h, and pH=6.8 phosphoric acid buffer solution is selected as the release medium within 2 h-8 h.

Evaluation method for the absorption and utilization rate in cells of the product in the present disclosure is: using Caco2 cell line for this study. Cells in the logarithmic growth phase are uniformly inoculated into a 100 mm cell culture dish for subsequent cell uptake experiments. All experiments are performed using Caco2 cells in the 20th generation. The sample to be tested is dissolved in sterile dimethyl sulfoxide (DMSO) and vortex mixed, the cell culture medium is used to gradient dilute to 20 μM, and then medicine is added to culture the cell. In the blank control group, cells are cultured with normal cell culture medium. After being treated with drugs, the cells are cultured in a $CO_2$ incubator for 24 h. Cells are collected, and 3 mL lysate is used to lyse the cells. Pigment is extracted with 3 mL tetrahydrofuran and 3 mL absolute ethanol. Absorbance is detected at the wavelength of 446 nm (lutein)/453 nm (zeaxanthin)/455 nm (β-carotene) by ultraviolet spectrophotometer, the absorbance is substituted into the standard curve to calculate the content of carotenoid in cells.

Determination of chiral isomerism of zeaxanthin in the present disclosure: detecting according to USP43, Meso-Zeaxanthin STEREOISOMERIC COMPOSITION.

Embodiment B1: Effect of Processing Method of Crystal on Stability of Crystal The specific content of the embodiment B1 is the same as that of the embodiment A1, please refer to the foregoing description for details.

Embodiment B2

The treated lutein crystal is obtained by mixing 200 g lutein crystal with 3 times of 60% ethanol aqueous solution, stirring at 45° C. for 30 min, then dispersing through high-speed shearing at 10,000 rpm, adding 20 g ascorbic acid, 1 g ascorbyl palmitate, and 1 g sucrose fatty acid ester, and removing the solvent at 75° C., and the treated lutein crystal is frozen at −20° C. for standby. The ethanol soluble residue of the treated lutein crystal is 7 ppm, and the moisture content of the treated lutein crystal is 10%. An aqueous solution with a solid content of 50% is prepared using 583 g sodium starch octenyl succinate and 195 g glucose. The aqueous solution is heated up to 90° C. and stirred at a constant speed for 35 min after stirring and dispersing at 60° C. The aqueous solution is cooled down to 60° C. and stirred for 100 min. The lutein product A is obtained by mixing the gelling wall material and the treated lutein crystal, stirring, emulsifying, and spray-drying, the pigment dissolution rate of which is 3.1%, and the release rates of which are 30.5% in 30 min and 103.3% in 4 h, respectively. The release rate of the lutein product A at different times is shown in Table 4 below.

TABLE 4

| Release rate at different times | | | |
|---|---|---|---|
| Time | Release rate | Time | Release rate |
| 10 min | 10.0% | 2 h 10 min | 89.4% |
| 20 min | 16.0% | 3 h | 101.6% |
| 30 min | 30.5% | 4 h | 103.3% |
| 1 h | 40.2% | 6 h | 101.6% |
| 2 h | 45.5% | 8 h | 101.6% |

Embodiment B3

The treated β-carotene crystal is obtained by mixing 233 g β-carotene crystal with 5 times of 50% ethanol aqueous solution, stirring at 40° C. for 40 min, then dispersing through high-speed shear at 10,000 rpm, adding 17 g ascorbic acid, 25.5 g ascorbyl palmitate, and 25.5 g sucrose fatty acid ester, and removing the solvent at 70° C., and the treated β-carotene crystal is frozen at −20° C. for standby. The ethanol soluble residue of the β-carotene crystal is 5 ppm, and the moisture content of the β-carotene crystal is 15%. An aqueous solution with a solid content of 70% is prepared using 560 g sodium starch octenyl succinate and 140 g glucose. After stirring and dispersing at 50° C., the aqueous solution is heated up to 80° C., stirred at a constant speed for 50 min, cooled down to 65° C., and stirred for 120 min. The β-carotene product A is obtained by mixing the gelling wall material with the treated β-carotene crystal, stirring, emulsifying, and spray-drying, the pigment dissolution rate of which is 2.3%, and release rates of which are 28.3% in 30 min and 100.2% in 4 h. The release rate of the β-carotene product A at different times is shown in Table 5 below.

TABLE 5

| Release rate at different times | | | |
|---|---|---|---|
| Time | Release rate | Time | Release rate |
| 10 min | 7.9% | 2 h 10 min | 82.9% |
| 20 min | 15.1% | 3 h | 101.6% |
| 30 min | 25.3% | 4 h | 100.2% |
| 1 h | 39.4% | 6 h | 101.6% |
| 2 h | 42.5% | 8 h | 102.2% |

Embodiment B4

The treated composite crystal is obtained by mixing 106 g β-carotene crystal, 212 g lutein ester crystal, 106 g zeaxanthin crystal, and 4 times of 70% ethanol aqueous solution, stirring at 50° C. for 55 min, and then dispersing through high-speed shear at 10,000 rpm, adding 73 g ascorbic acid, 1.5 g ascorbyl palmitate, and 1.5 g sucrose fatty acid ester, and removing solvent at 80° C., and the treated composite crystal is frozen at −20° C. for standby. The ethanol soluble residue in the treated composite crystal is 3 ppm, and the moisture content of the treated composite crystal is 30%. An aqueous solution with a solid content of 60% is prepared using 416.7 g sodium starch octenyl succinate and 83.3 g glucose syrup. After stirring and dispersing at 70° C., the aqueous solution is heated up to 85° C., stirred at a constant speed for 45 min, cooled down to 63° C., and stirred for 130 min. The product A with a ratio of lutein ester, zeaxanthin, and β-carotene of 2:1:1 by mixing the gelling wall material with the treated composite crystal, stirring, emulsifying, and spray-drying, the pigment dissolution rate of which is 3.5%, and the release rates of which are 22.4% in 30 min and 99.7% in 4 h. The release rate of the product A with a ratio of lutein ester, zeaxanthin, and β-carotene of 2:1:1 at different times is shown in Table 6 below.

TABLE 6

| Release rate at different times | | | |
|---|---|---|---|
| Time | Release rate | Time | Release rate |
| 10 min | 10.2% | 2 h 10 min | 79.9% |
| 20 min | 17.2% | 3 h | 97.0% |
| 30 min | 28.3% | 4 h | 99.7% |
| 1 h | 41.4% | 6 h | 99.9% |
| 2 h | 46.4% | 8 h | 99.7% |

It can be seen from embodiments B2-B4 that the carotenoid crystal is obtained by using 3-5 times of 50%-70% ethanol aqueous solution to mix carotenoid, stirring, high-speed shear dispersion, adding antioxidant, and removing the solvent, the ethanol soluble residue of the carotenoid crystal is less than 10 ppm, and the moisture content of the carotenoid crystal is within a range of 10%-30%. An aqueous solution with a solid content of 50-70% is prepared using at least starch as the wall material, and mixing the wall material and carbohydrate in a weight ratio of (1-5):1, and the pretreated gelling wall material is obtained by stirring and dispersing. The carotenoid preparation is prepared by mixing the treated carotenoid crystal with the gelling wall material. The pigment dissolution rate of the carotenoid preparation is less than 5%, and it is not easy to cause staining of clothes, tongue, etc. during the use of the carotenoid preparation. Moreover, the release rate of the carotenoid preparation in the hydrochloric acid solution for 0.5 h is less than 35%, which may effectively protect the carotenoid from being destroyed in the stomach, and the release rate of the carotenoid in phosphate buffer solution for 4 h is greater than 90%, which is conducive to subsequent intestinal absorption.

Comparative Embodiment B5

The treated β-carotene crystal is obtained by mixing 200 g β-carotene crystal with 3 times of 60% ethanol aqueous solution, stirring at 45° C. for 30 min, and then dispersing through high-speed shearing at 10,000 rpm, adding 20 g ascorbic acid, 1 g ascorbyl palmitate, and 1 g sucrose fatty acid ester, and removing the solvent at 75° C., and the treated β-carotene crystal is frozen at −20° C. for standby. The ethanol soluble residue in the treated β-carotene crystal is 7 ppm, and the moisture content of the treated β-carotene crystal is 12.8%. The β-carotene product B is obtained by preparing an aqueous solution with 50% solid content using 583 g starch sodium octenylsuccinate and 195 g glucose, stirring and dissolving at 60° C., then adding the β-carotene crystal, stirring, emulsifying, and spray drying, the pigment dissolution rate of which is 65.8%, and the release rates of which are 99.1% in 30 min and 98.9% in 4 h.

Compared with embodiments B2-B4, as the wall material of comparative embodiment B5 is not undergone gelling treatment (without heating, stirring and cooling treatment to make the wall material gelling), the pigment dissolution rate of the product prepared by the comparative embodiment B5 increases, and the release rate of the product in hydrochloric acid solution increases, which may leads to the destruction of carotenoid in gastric juice and can not be well absorbed into the intestinal tract, and the effect of which becomes worse.

Comparative Embodiment B6

The treated lutein ester crystal is obtained by mixing 200 g lutein ester crystal with 3 times of 60% ethanol aqueous solution, stirring at 45° C. for 30 min, and then dispersing through high-speed shearing at 10,000 rpm, adding 20 g ascorbic acid, 1 g ascorbyl palmitate, and 1 g sucrose fatty acid ester, and removing the solvent at 75° C., and the treated lutein ester crystal is frozen at −20° C. for standby. The ethanol soluble residue in the treated lutein ester crystal is 5.3 ppm, and the moisture content of the treated lutein ester crystal is 25%. An aqueous solution with a solid content of 50% is prepared using 583 g sodium starch octenyl succinate and 195 g glucose, the aqueous solution is heated up to 100° C. and stirred at a constant speed for 60 min after stirring and dispersing at 60° C. The lutein ester product A is obtained by mixing the gelling wall material and the treated lutein ester crystal, stirring, emulsifying and spray-drying, the pigment dissolution rate of which is 85.2%, and the release rates of which are 97.7% in 30 min and 102.3% in 4 h.

Compared with embodiments B2-B4, for comparative embodiment B6, the wall material is treated under condition (after stirring and dispersing at 60° C., heating up to 100° C. and evenly stirring for 60 min) other than the gelling method in the preparation method described in this disclosure, the pigment dissolution rate of the product prepared by the comparative embodiment B6 increases, and the release rate of the product in hydrochloric acid solution increases, which may lead to the destruction of carotenoid in gastric juice and can not be well absorbed into the intestinal tract, and the effect of which becomes worse.

Comparative Embodiment B7

The mixed lutein crystal is obtained by mixing 200 g lutein crystal, 20 g ascorbic acid, 1 g ascorbyl palmitate, and 1 g sucrose fatty acid ester. An aqueous solution with a solid content of 50% is prepared using 583 g sodium starch octenyl succinate and 195 g glucose syrup, after stirring and dispersing at 60° C., the aqueous solution is heated up to 90° C., stirred at a constant speed for 35 min, cooled down to 60° C., and stirred for 100 min. The lutein product B is obtained by mixing the gelling wall material and the mixed lutein crystal, stirring, emulsifying, and spray-drying, the pigment dissolution rate of which is 33.2%, and the release rates of which are 90.1% in 30 min and 95.5% in 4 h. Compared with embodiments B2-B4, the lutein crystal of comparative embodiment B7 is not pretreated (lutein crystal is not mixed and stirred with ethanol solution, and pretreated with high-speed shear dispersion and solvent removal), so the pigment dissolution rate of the product prepared by the comparative embodiment B7 increases, and the release rate of the product in hydrochloric acid solution increases, which may lead to the destruction of carotenoid in gastric juice and can not be well absorbed into the intestinal tract, and the effect of which becomes worse.

Comparative Embodiment B8

The treated lutein crystal is obtained by mixing 200 g lutein crystal with 3 times of 60% ethanol aqueous solution, stirring at 45° C. for 30 min, and then dispersing through high-speed shearing at 10,000 rpm, adding 20 g ascorbic acid, 1 g ascorbyl palmitate, and 1 g sucrose fatty acid ester, and removing the solvent at 75° C., and the treated lutein crystal is frozen at −20° C. for standby. The ethanol soluble residue of the treated lutein crystal is 7 ppm, and the moisture content of the treated lutein crystal is 10%. An aqueous solution with a solid content of 50% is prepared using 583 g cornstarch and 195 g glucose, and after stirring and dispersing at 60° C., the aqueous solution is heated up to 90° C., stirred at a constant speed for 35 min, cooled down to 60° C., and stirred for 100 min. The lutein product C is obtained by mixing the gelling wall material with the treated lutein crystal, stirring, emulsifying, and spray-drying, the pigment dissolution rate of which is 73.5%, and the release rates of which are 99.5% in 30 min and 101.3% in 4 h.

Compared with embodiments B2-B4, for comparative embodiment B8, starch sodium octenylsuccinate is replaced with corn starch, the pigment dissolution rate of the product prepared by the comparative embodiment B8 increases, and the release rate of the product in hydrochloric acid solution increases, which may lead to the destruction of carotenoid in gastric juice and can not be well absorbed into the intestinal tract, and the effect of the product becomes worse, indicating that the effect of the product prepared by the embodiments B2-B4 using starch sodium octenylsuccinate as the wall material is better.

Effect Embodiment B9

The composite product 3 is obtained by the weight ratio of lutein, zeaxanthin, and (3-carotene of 1:1:1, and the lutein is prepared using the method of patent CN108185424B (Patent Application No. CN201711456450.1). The composite product 4 is obtained by the weight ratio of lutein, zeaxanthin, and β-carotene of 1:1:1, and the lutein is prepared using the method of embodiment B2. The comparison parameters of the two products are shown in Table 7 below.

TABLE 7

Comparison parameters of two products

| Product | Bulk density | Retention rate for accelerating 6 months at 40° C. | Pigment dissolution rate | Release rate 30 min | Release rate 4 h |
|---|---|---|---|---|---|
| Composite product 3 | 0.65 | 99.5% | 68.2% | 95.1% | 102.3% |
| Composite product 4 | 0.63 | 99.6% | 3.4% | 25.9% | 98.2% |

Through the comparison of the composite product 3 and the composite product 4, it can be seen that the pigment dissolution rate of composite product 4 prepared through the preparation process of this disclosure (embodiment B2) is lower than that of the composite product 3 prepared according to the preparation method of the patent CN108185424B, and the release rate of composite product 4 prepared through the preparation process of this disclosure (embodiment B2) is lower than that of the composite product 3 prepared according to the preparation method of the patent CN108185424B. The release rate of the composite product 4 in hydrochloric acid solution (in 30 min) is significantly lower than that of the composite product 3, indicating that composite product 4 can effectively protect carotenoid from being destroyed by gastric juice in the stomach. However, the release rate of the composite product 4 in phosphate buffer solution (in 4 h) is 98.2%, indicating that composite product 4 can be well absorbed after entering the intestinal tract, and the application effect of the composite product 4 is better.

Effect Embodiment B10: Application Evaluation of Soft Candy

The solution II is obtained by weighing 8 g gelatin, 44 g white sugar, and 55 g glucose syrup, adding water with 20% solid content, stirring and dissolve, boiling the sugar at 120° C. until the solid content is about 85%, and adjusting the pH=3-4.

Figure 4A:
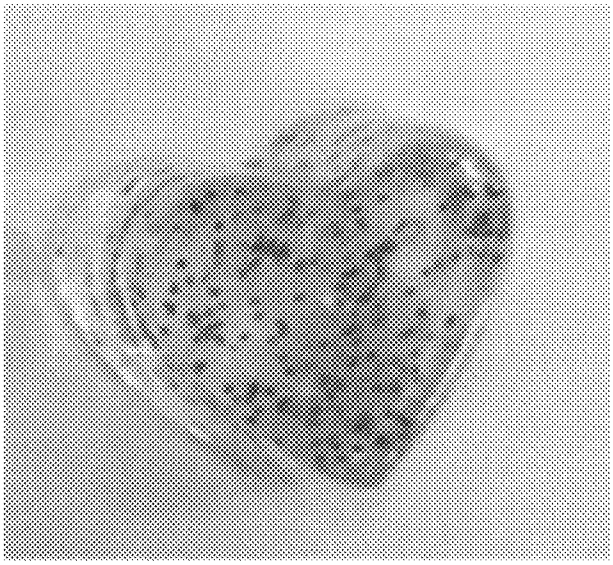
FIG. 4A is an exemplary appearance diagram of a soft candy of lutein product A according to some embodiments of the present disclosure.
Figure 4B:
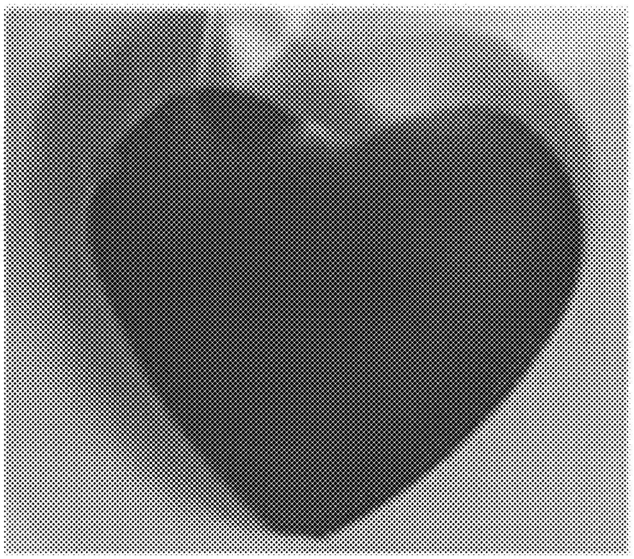
FIG. 4B is an exemplary appearance diagram of β-carotene product B according to some embodiments of the present disclosure.

20 g the lutein product A prepared according to the method of embodiment B2 or 20 g the β-carotene product B prepared according to the method of comparative embodiment B5 into the solution II, and the obtained solution is stirred evenly, and kept at 90° C. for 40 min. The soft candy of lutein product A and the soft candy of β-carotene product B are obtained by injection molding and drying, and the appearance of which is shown in FIG. 4A and FIG. 4B respectively. It can be seen that the lutein product A has no staining phenomenon in the soft candy, and is completely preserved in the soft candy, realizing the effect of nutritional visualization. However, the β-carotene product B dyes the soft candy red, and the transparency of the soft candy decreases.

Effect Embodiment B11: Application Evaluation of Solid Drinks

The lutein product A prepared by the method of embodiment B2 and the β-carotene product B prepared by the method of comparative embodiment B5 are respectively mixed with an appropriate amount of 0.03% of citric acid, 20% of maltodextrin, 0.6% of xanthan gum, etc. to made into a solid drink and evaluation is performed after brewing. The evaluation of the two products is as follows in Table 8.

TABLE 8

Comparison parameters of two products

| Number of solid drink | Condition of staining tongue | Texture |
|---|---|---|
| Lutein product A | Insoluble and suspended in water, and not staining tongue after drinking | Moderate acidity and sweetness, and no foreign body sensation |
| B-carotene product B | Dispersing and dissolving in water, and staining tongue as yellow after drinking | Moderate acidity and sweetness, and no other discomfort |

Through the comparison of the solid drink made by lutein product A (prepared by the method of embodiment B2) and β-carotene product B (prepared by the method of comparative embodiment B5), it can be seen that the solid drink made by lutein product A do not dye the tongue, and its application effect is better.

Effect Embodiment B12: Comparison of Bioavailability of Lutein

Figure 5:
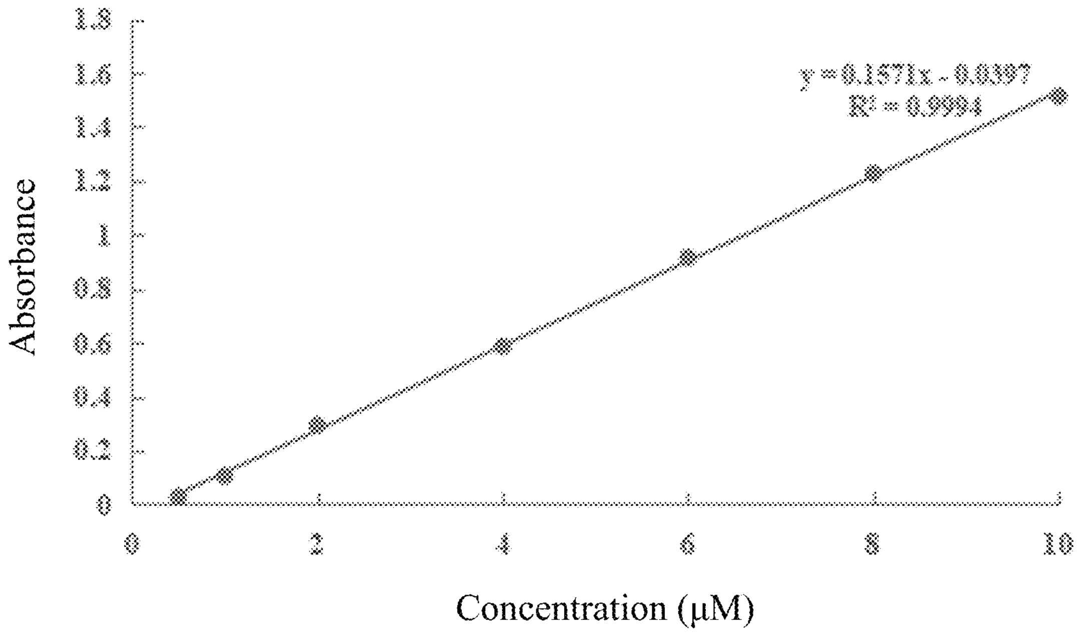
FIG. 5 is an exemplary curve illustrating absorbance of standard solutions of lutein with different concentrations according to some embodiments of the present disclosure.
Figure 6:
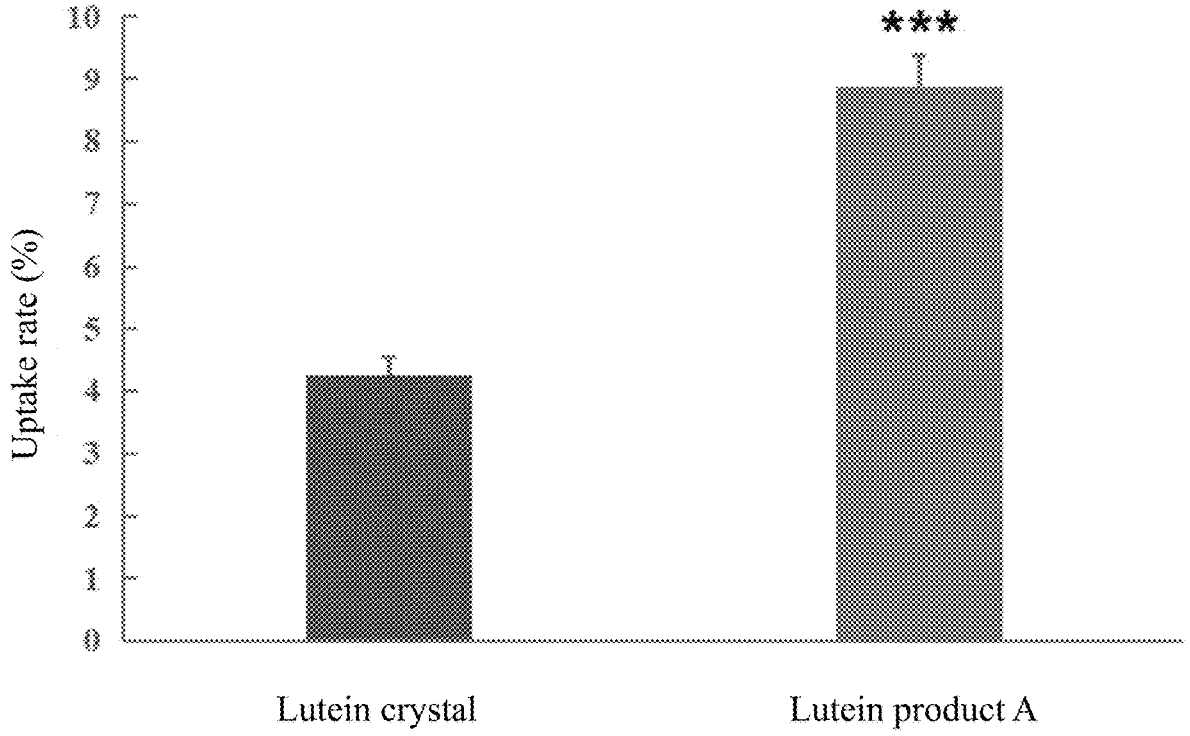
FIG. 6 is an exemplary bar graph of cellular uptake rates of lutein crystal and lutein product A according to some embodiments of the present disclosure.

Lutein standard solution with 0.5, 1, 2, 4, 6, 8, and 10 μM is prepared, and the absorbance of the lutein standard solution at a wavelength of 446 nm is detected by an ultraviolet spectrophotometer. The standard curve is drawn using the concentration (μM) as the abscissa and the absorbance as the ordinate, as shown in FIG. 5. Solution with 20 μM are prepared using the lutein product A (XanGuard® lutein microparticle 10% GF) prepared by the method in embodiment B2 and lutein crystal, and the Caco2 cell are treated for 24 h, and the cell uptake rate is compared, as shown in FIG. 6 (n=3, *p<0.05, p<0.01, *p<0.001). The results show that, compared with the lutein crystal group, the lutein product group A significantly increases the cell uptake rate and its cell uptake rate is 2.1 times that of the lutein crystal group. It is proved that the product prepared by the disclosure improves the bioavailability of lutein.

Effect Embodiment B13: Comparison of Bioavailability of Zeaxanthin

Figure 7:
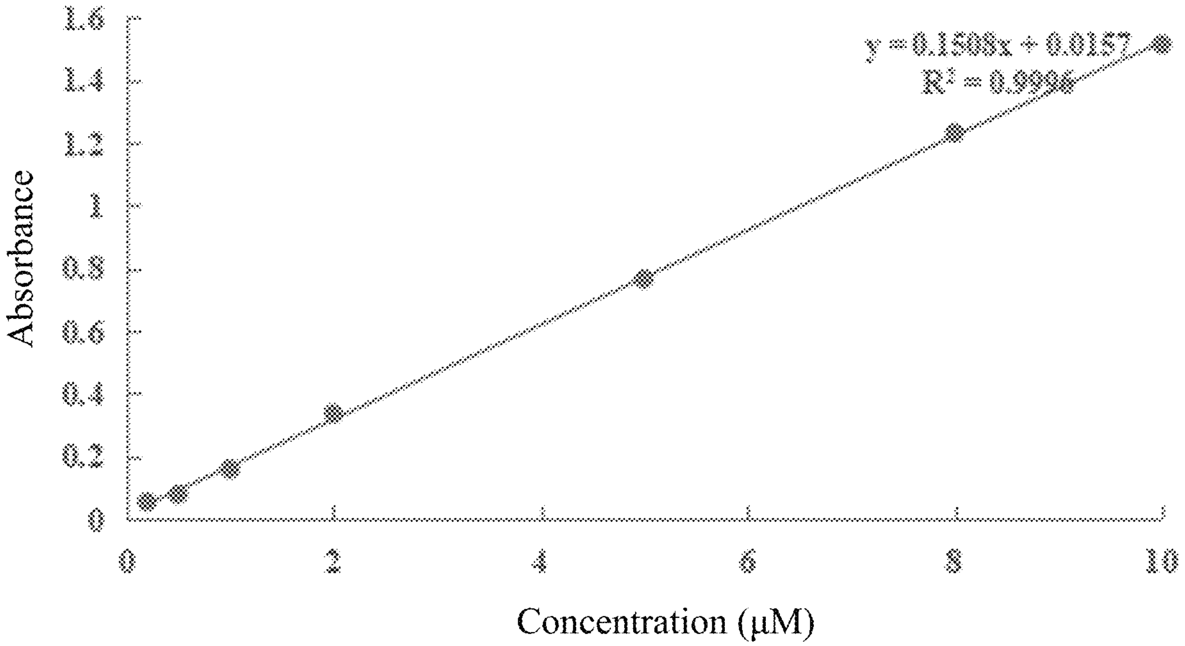
FIG. 7 is an exemplary curve of the absorbance of standard solutions of zeaxanth with different concentrations according to some embodiments of the present disclosure.
Figure 8:
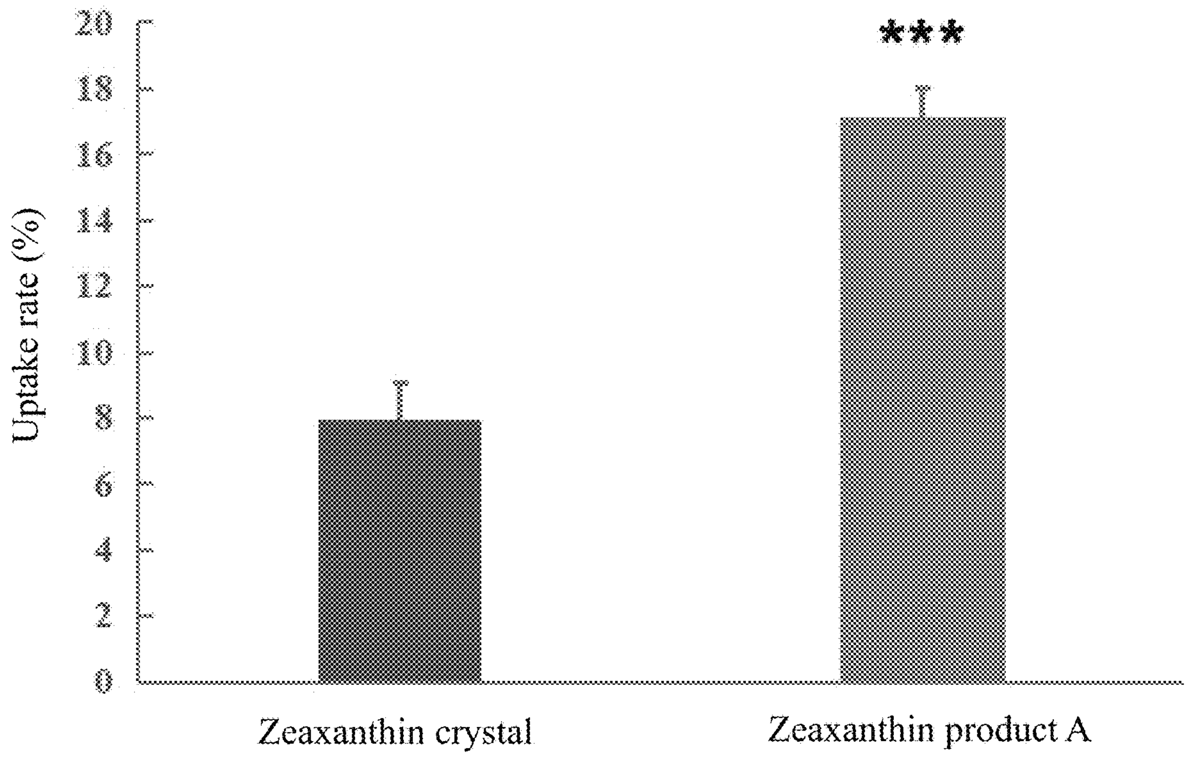
FIG. 8 is an exemplary bar graph of cellular uptake rates of zeaxanthin crystal and zeaxanthin product A according to some embodiments of the present disclosure.

Standard solutions with 0.2, 0.5, 1, 2, 5, 8, and 10 μM are prepared using the zeaxanthin, and the absorbance of the standard solution at a wavelength of 453 nm is detected by an ultraviolet spectrophotometer. The standard curve is drawn using the concentration (11M) as the abscissa and the absorbance as the ordinate, as shown in FIG. 7. Solutions with 20 μM are prepared using the zeaxanthin product A (XanGuard® zeaxanthin microparticles 5% GF) prepared by the method in Embodiment B2 and zeaxanthin crystal, and the Caco2 cells are treated for 24 h, and their cell uptake rates are compared, as shown in FIG. 8 (n=3, *p<0.05, p<0.01, *p<0.001). The results showed that, compared with the zeaxanthin crystal group, the zeaxanthin product group A significantly increases the cellular uptake rate and its cellular uptake rate is 2.2 times that of the zeaxanthin crystal group. It is proved that the product prepared by the disclosure improves the bioavailability of zeaxanthin.

Figure 9:
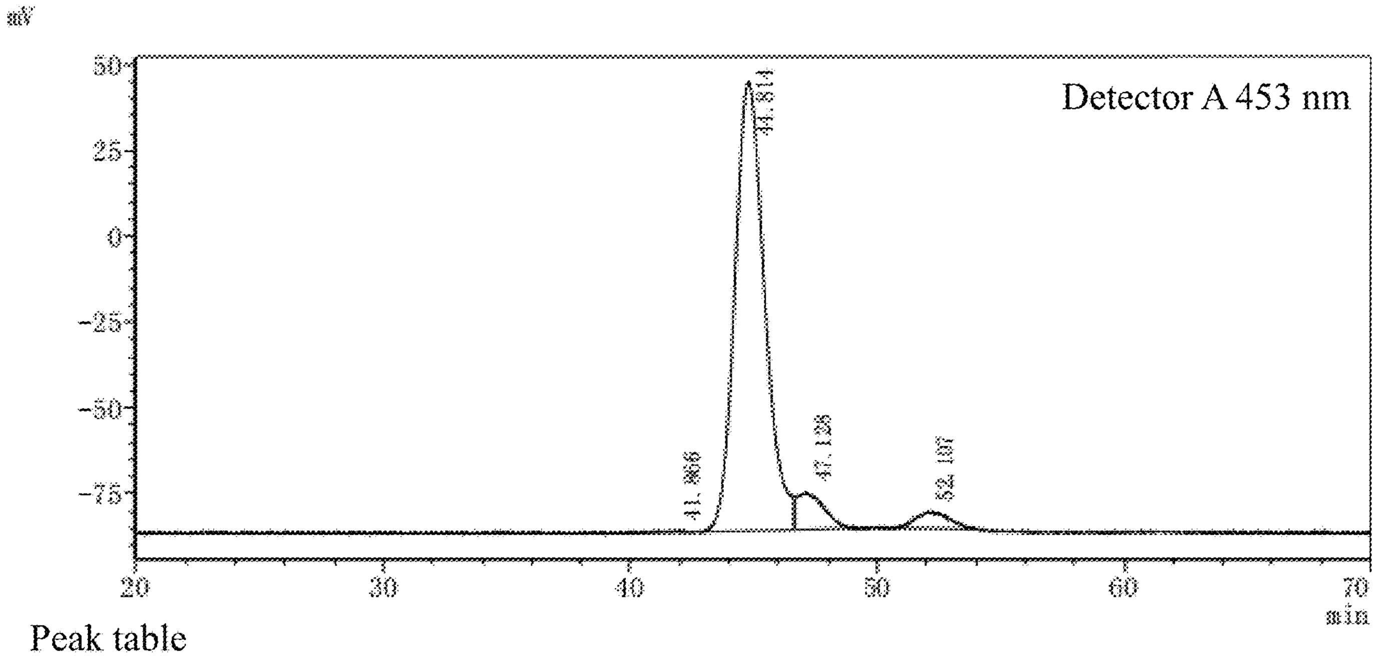
FIG. 9 is an exemplary diagram of detection result of chiral structure of zeaxanthin according to some embodiments of the present disclosure.

The zeaxanthin used in this embodiment includes two isomers of (3R, 3'R)-zeaxanthin and (3R, 3'S)-zeaxanthin, and the two isomers account for more than 80% by weight of zeaxanthin; and when the weight ratio between two isomers of (3R, 3'R)-zeaxanthin and (3R, 3'S)-zeaxanthin is within a range of (5-15%):(95-85%), zeaxanthin does not affect the absorption of zeaxanthin cells. The detection results of the chiral structure of zeaxanthin in samples absorbed by cells are shown in FIG. 9. The results showed that after zeaxanthin is absorbed by Caco2 cells, it still exists in the form of mesosomes in the cells and is not transformed into other forms. It shows that there is no specific selection of (3R, 3'R)-zeaxanthin or (3R,3'S)-zeaxanthin for cell absorption.

The above is only a preferred embodiment of the present disclosure, but the scope of protection of the present disclosure is not limited thereto. Changes or replacements that can easily be thought of by those skilled in the art within the technical scope disclosed by the disclosure should be included in the protection scope of the disclosure. Therefore, the protection scope of the present disclosure should be determined by the protection scope of the claims.

In some embodiments, carotenoid may include lutein. At present, the traditional process generally adopts saponification to prepare lutein, but a large amount of alkali is used in the preparation process, resulting in alkaline wastewater, which is not friendly to the environment, and the purity of lutein in the prepared product is low.

In some embodiments of this disclosure, the marigold extract solution is obtained by mixing the marigold extract with the lower alcohol, and then the marigold extract solution and the alcohol-mixed solution are respectively input into the preheating pipeline, and the reaction flow rate ratio is controlled. The saponification reaction is carried out at a certain temperature and pressure, the acid is added into the saponified reaction solution for neutralization, the complexing agent is added into the saponified reaction solution for extracting lutein, and the lutein crystal is obtained after subsequent treatment. In the process, the tubular reaction is used to preheat reaction raw material and mixed reaction raw material in advance, which can realize the continuous reaction of lutein preparation and greatly shorten the reaction time. At the same time, the alcoholysis method is used to convert lutein ester into lutein with only a small amount of alkali. In addition, the complexing method is used to directly separate lutein, the content and yield of the separated lutein are high, and the reaction time is short.

Figure 10:
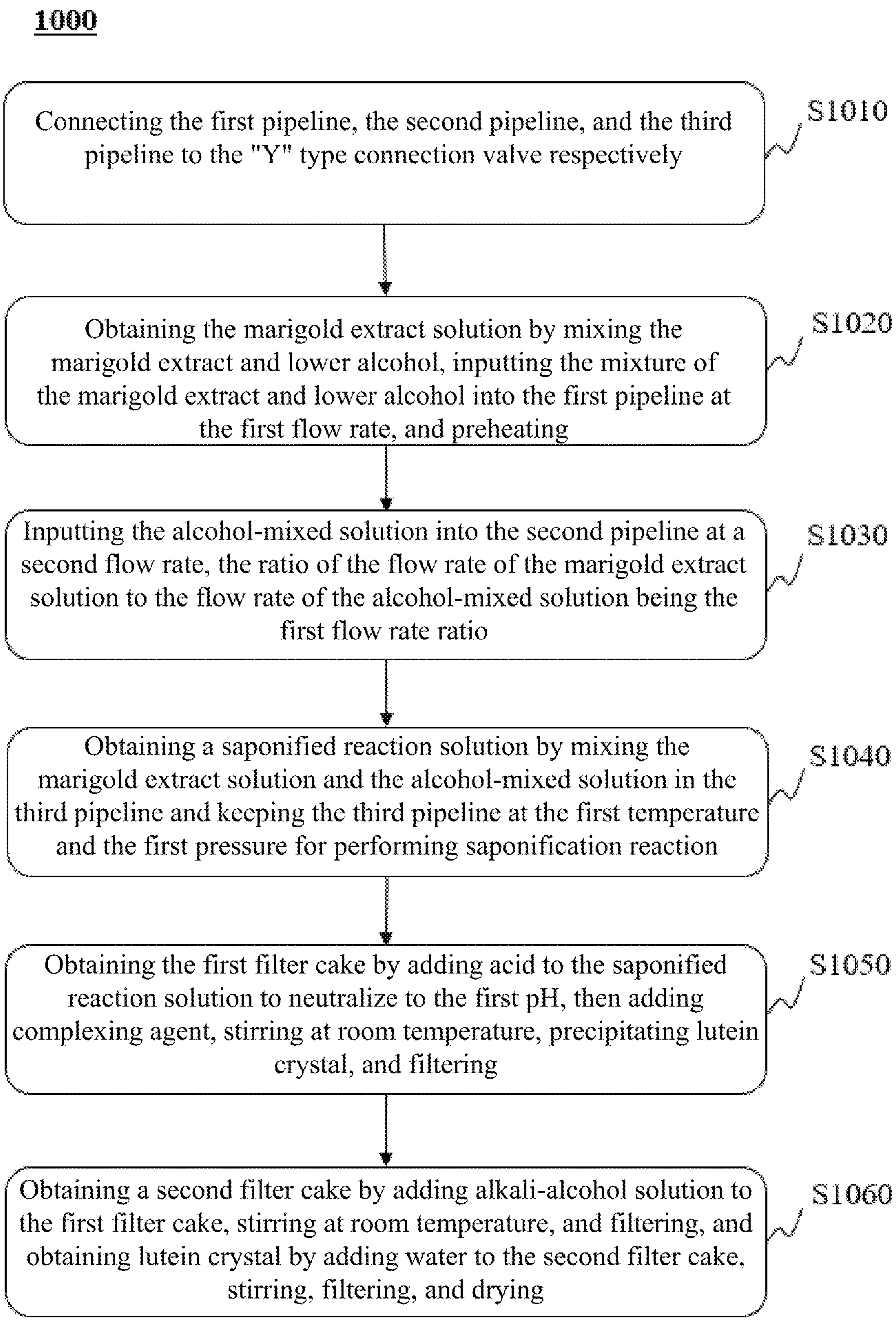
FIG. 10 is an exemplary flowchart illustrating a process of a method for preparing lutein according to some embodiments of the present disclosure.

FIG. 10 is a flowchart illustrating a process of a method for preparing lutein according to some embodiments of the present disclosure. Process 1000 may include the following steps.

Step S1010: connecting the first pipeline, the second pipeline, and the third pipeline to the "Y" type connection valve respectively.

Figure 11:
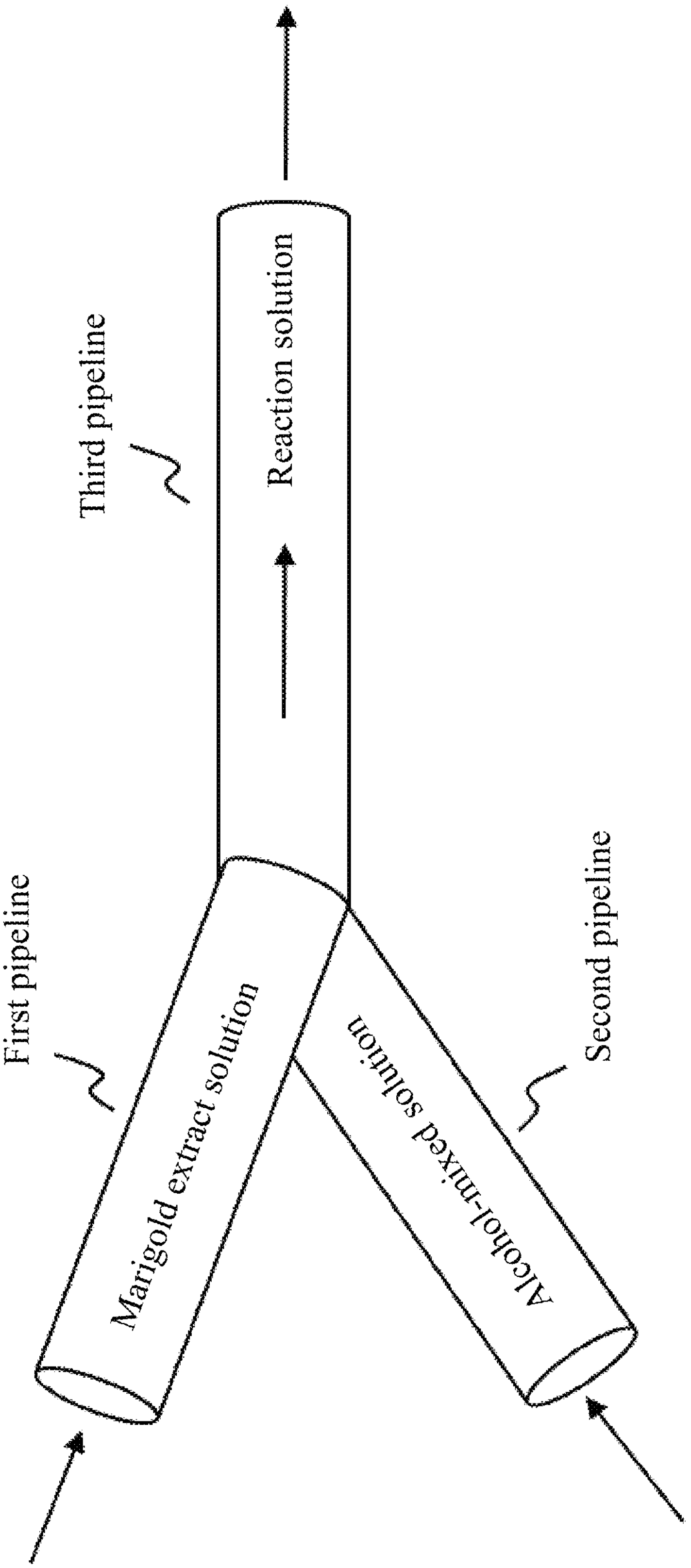
FIG. 11 is an exemplary schematic diagram of a "Y" type connection valve connecting a pipeline according to some embodiments of the present disclosure.

In some embodiments, the first pipeline and the second pipeline may be preheating pipelines for transporting reaction raw material. As shown in FIG. 11, the first pipeline may be used to transport the marigold extract solution, and the second pipeline may be used to transport the alcohol-mixed solution. In some embodiments, the third pipeline is used for mixing reaction raw material and performing saponification reaction. In some embodiments, the first pipeline and the second pipeline may be straight pipes or coil pipes. In some embodiments, the diameter of the first pipeline and the diameter of the second pipeline may be within a range of 0.2 cm-2 cm. In some embodiments, the diameter of the first pipeline and the diameter of the second pipeline may be within a range of 0.5 cm-1.6 cm. In some embodiments, the diameter of the first pipeline and the diameter of the second pipeline may be within a range of 1.0 cm-1.5 cm. In some embodiments, the length of the first pipeline and the length of the second pipeline may be within a range of 0.5 m-3 m. In some embodiments, the length of the first pipeline and the length of the second pipeline may be within a range of 1.5 m-2.5 m. In some embodiments, the length of the first pipeline and the length of the second pipeline may be within a range of 2 m-2.5 m. In some embodiments, the third pipeline may be a straight pipe or a coil pipe. In some embodiments, the diameter of the third pipeline may be within a range of 1.2 cm-1.6 cm. In some embodiments, the diameter of the third pipeline may be within a range of 1.0 cm-1.5 cm. In some embodiments, the diameter of the third pipeline may be within a range of 0.7 cm-0.9 cm. In some embodiments, the length of the third pipeline may be within a range of 30 m-100 m. In some embodiments, the length of the third pipeline may be within a range of 3 m-60 m. In some embodiments, the length of the third pipeline may be within a range of 9 m-20 m.

Step S1020: obtaining the marigold extract solution by mixing the marigold extract and lower alcohol, inputting the mixture of the marigold extract and lower alcohol into the first pipeline at the first flow rate, and preheating.

In some embodiments, the lower alcohol may be C1-C4 of lower alcohol. In some embodiments, the lower alcohol may be at least one of anhydrous methanol, ethanol, isopropanol, and n-butanol. In some embodiments, the mass ratio of marigold extract to lower alcohol is within a range of 1:(2-10). In some embodiments, the mass ratio of marigold extract to lower alcohol is within a range of 1:(3-8). In some embodiments, the mass ratio of marigold extract to lower alcohol is within a range of 1:(5-7).

The first flow rate is the flow rate of the mixed solution of marigold extract and lower alcohol (i.e., marigold extract solution). In some embodiments, the first flow rate may be within a range of 2 mL/min-800 mL/min. In some embodiments, the first flow rate may be within a range of 50 mL/min-600 mL/min. In some embodiments, the first flow rate may be within a range of 100 mL/min-500 mL/min. In some embodiments, the first flow rate may be within a range of 200 mL/min-400 mL/min. In some embodiments, the first flow rate may be within a range of 250 mL/min-300 mL/min.

The preheating temperature may refer to the temperature at which the reaction raw material in the preheating pipeline (i.e., the first pipeline and the second pipeline) are heated. In some embodiments, the preheating temperature may be within a range of 60° C.-100° C. In some embodiments, the preheating temperature may be within a range of 70° C.-90° C. In some embodiments, the preheating temperature may be within a range of 80° C.-85° C.

Step S1030: inputting the alcohol-mixed solution into the second pipeline at a second flow rate, the ratio of the flow rate of the marigold extract solution to the flow rate of the alcohol-mixed solution being the first flow rate ratio.

The second flow rate is the flow rate of the alcohol-mixed solution entering the second pipeline. In some embodiments, the second flow rate may be within a range of 2 mL/min-1200 mL/min. In some embodiments, the second flow rate may be within a range of 50 mL/min-1000 mL/min. In some embodiments, the second flow rate may be within a range of 100 mL/min-800 mL/min. In some embodiments, the second flow rate may be within a range of 300 mL/min-600 mL/min. In some embodiments, the second flow rate may be within a range of 400 mL/min-500 mL/min.

In some embodiments, the mass concentration of the alcohol-mixed solution may be within a range of 0.01%-8%. In some embodiments, the mass concentration of the alcohol-mixed solution may be within a range of 0.1%-0.7%. In some embodiments, the mass concentration of the alcohol-mixed solution may be within a range of 0.3%-0.5%. In some embodiments, the alcohol-mixed solution may include at least one of sodium ethoxide ethanol solution, sodium methoxide methanol solution, potassium methoxide methanol solution, potassium ethoxide ethanol solution, sodium hydroxide alcohol solution, and potassium hydroxide alcohol solution.

The first flow rate ratio refers to the ratio of the flow rate of the marigold extract solution to the flow rate of the alcohol-mixed solution when the reaction raw material enters the third pipeline. In some embodiments, the first flow rate ratio may be within a range of 1:(1-5). In some embodiments, the first flow rate ratio may be within a range of 1:(2-4). In some embodiments, the first flow rate ratio may be within a rang of 1:(3-4). For example, when the flow rate of marigold extract solution is 150 mL/min, the flow rate of alcohol-mixed solution is 250 mL/min.

Step S1040: obtaining a saponified reaction solution by mixing the marigold extract solution and the alcohol-mixed solution in the third pipeline and keeping the third pipeline at the first temperature and the first pressure for performing saponification reaction.

FIG. 11 is a schematic diagram of the "Y" type connection valve connecting pipeline in some embodiments of present disclosure. In some embodiments, as shown in FIG. 11, the marigold extract solution in the first pipeline and the alcohol-mixed solution in the second pipeline are mixed in the third pipeline after passing through the "Y" type connection valve, and the mixed marigold extract solution and the alcohol-mixed solution are saponified in the third pipeline at the first temperature and the first pressure to obtain a saponified reaction solution.

In some embodiments, the first temperature may be within a range of 60° C.-120° C. In some embodiments, the first temperature may be within a range of 80° C.-110° C. In some embodiments, the first temperature may be within a range of 90° C.-100° C. In some embodiments, the first pressure may be within a range of 0-5 MPa. In some embodiments, the first pressure may be within a range of 0.5 MPa-4 MPa. In some embodiments, the first pressure may be within a range of 1 MPa-3 MPa.

The reaction raw material of marigold extract solution and alcohol-mixed solution are preheated through the first pipeline and the second pipeline respectively, and then enter the third pipeline for mixing and performing saponification reaction, marigold extract solution and alcohol-mixed solution may be saponified rapidly under high temperature to obtain lutein, so as to realize continuous reaction to prepare lutein. In addition, the "Y" type connection valve is used to connect three pipelines for mixed reaction, which can effectively shorten the saponification time, reduce manual operations, and reduce labor costs.

Step S1050: obtaining the first filter cake by adding acid to the saponified reaction solution to neutralize to the first pH, then adding complexing agent, stirring at room temperature, precipitating lutein crystal, and filtering.

In some embodiments, the acid used to neutralize may include at least one of glacial acetic acid, sulfuric acid, phosphoric acid, citric acid, hydrochloric acid, sodium dihydrogen phosphate, and potassium dihydrogen phosphate. In some embodiments, the mass ratio of acid to marigold extract is within a range of (5-10):1. In some embodiments, the mass ratio of acid to marigold extract is within a range of (6-9):1. In some embodiments, the mass ratio of acid to marigold extract is within a range of (7-8):1. In some embodiments, the first pH may be within a range of 4-8. In some embodiments, the first pH may be within a range of 6-8. In some embodiments, the first pH may be within a range of 5-7.

In some embodiments, the complexing agent may be tributyl phosphate or trioctylamine. In some embodiments, the mass ratio of complexing agent to marigold extract may be within a range of (0.0005-0.01):1. In some embodiments, the mass ratio of complexing agent to marigold extract may be within a range of (0.0005-0.005):1. In some embodiments, the mass ratio of complexing agent to marigold extract may be within a rang of (0.001-0.0025):1.

Lutein crystal with high purity may be obtained by purifying with complexing agent after saponification reaction, which improves the yield of lutein crystal, and does not use other organic solvents for purification, so as to achieve preparation of lutein crystal with high purity in an environmentally friendly way.

Step S1060: obtaining a second filter cake by adding alkali-alcohol solution to the first filter cake, stirring at room temperature, and filtering, and obtaining lutein crystal by adding water to the second filter cake, stirring, filtering, and drying.

In some embodiments, the alkali in the alkali alcohol solution may include at least one of sodium hydroxide, potassium hydroxide, sodium carbonate, potassium carbonate, sodium bicarbonate, and potassium bicarbonate. In some embodiments, the alcohol in the alkali alcohol solution may include at least one of methanol or ethanol. In some embodiments, the mass concentration of the alkali alcohol solution may be within a range of 0.1%-2.0%. In some embodiments, the mass concentration of the alkali alcohol solution may be within a range of 0.1%-1.0%. In some embodiments, the mass of the alkali-alcohol solution is 0.5 times-5 times of the mass of the marigold extract. In some embodiments, the mass of the alkali alcohol solution is 1 time-4 times of the mass of the marigold extract. In some embodiments, the amount of the alkali-alcohol solution is 2 times-3 times of the mass of the marigold extract. In some embodiments, the mass of water added to the second filter cake may be 0.5 times-5 times of the mass of marigold extract. In some embodiments, the mass of water added to the second filter cake may be 1 time-4 times of the mass of marigold extract. In some embodiments, the mass of water added to the second filter cake may be 2 times-3 times of the mass of marigold extract. In some embodiments, the stirring time may be within a range of 20 min-60 min. In some embodiments, the stirring time may be within a range of 30 min-50 min. In some embodiments, the stirring time may be within a range of 40 min-45 min. In some embodiments, the drying temperature may be within a range of 30° C.-60° C. In some embodiments, the drying temperature may be within a range of 40° C.-50° C. In some embodiments, the drying temperature may be within a range of 40° C.-45° C.

The preparation method of lutein may be described in detail below through embodiments C1-C8 and comparative embodiments C1-C5. It should be noted that the reaction condition, reaction material, and the amount of reaction material in embodiments C1-C8 are only for illustrating the preparation method of lutein, and do not limit the protection scope of this description. Embodiments C1-C8 are embodiments using different reaction conditions and material weight ratios, comparative embodiment C1 is an embodiment that does not use a tubular reaction (three pipelines connected by a "Y" type connection valve), and comparative embodiment C2 is an embodiment that performing a tubular reaction without using three pipelines connected by a "Y" type connection valve, does not use an alcoholysis method or a complexing agent. Comparative embodiments C3-C5 are embodiments for preparing lutein by the method of other patent applications. Comparative embodiments C1-C5 are control groups for embodiments C1-C8.

Embodiment C1

(1) Two pipelines with a length of 2 m and a diameter of 0.8 cm are used as the first pipeline and the second pipeline, and the first pipeline and the second pipeline are connected to both ends of the "Y" type connector (or referred to as "Y" type connection valve), the other end of the "Y" type connector is connected to the third pipeline, and the third pipeline is a pipeline with a length of 9 m and a diameter of 0.8 cm.

(2) 200 kg marigold extract are taken, 800 kg absolute ethanol are added, and the marigold extract and the absolute ethanol are pumped into the first pipeline at a flow rate of 150 mL/min while stirring. 0.375 kg of sodium ethylate is taken to dissolve in 800 kg absolute ethanol, and the obtained solution is pumped into the second pipeline at a flow rate of 250 mL/min.

(3) The reaction temperature in the third pipeline is set as 85° C., the pressure in the third pipeline is set as 0.2 MPa to perform saponification reaction, and the reaction solution is received at the end of the third pipeline.

Experimental results: the liquid phase composition of the reaction solution is measured, the transesterification rate of the lutein ester in the marigold extract of the reactant reaches 99.4%, the remaining ratio of lutein ester is 0.6%, and the saponification time is 13 min.

Embodiment C2

(1) Two pipelines with a length of 2 m and a diameter of 0.8 cm are selected as the first pipeline and the second pipeline, and the first pipeline and the second pipeline are connected to both ends of the "Y" type connector (or referred to be as"Y" type connection valve), the other end of the "Y" type connector is connected to the third pipeline, and the third pipeline is a pipeline with a length of 54 m and a diameter of 1.4 cm.

(2) 20 kg marigold extract is taken, 60 kg absolute ethanol is added, and the obtained solution is pumped into the first pipeline at a flow rate of 200 mL/min while stirring. 0.75 kg of potassium ethylate is taken to dissolve in 80 kg absolute ethanol, and the solution is pumped into the second pipeline at a flow rate of 300 mL/min.

(3) The reaction temperature in the third pipeline is set as 85° C. and the pressure in the third pipeline is set as 0.2 MPa to perform saponification reaction, and the reaction solution at the end of the third pipeline is received.

Experimental results: the liquid phase composition of the reaction solution is measured, the transesterification rate of the lutein ester in the marigold extract of the reactant reaches 99.73%, the remaining ratio of lutein ester is 0.3%, and the saponification time is 8 min.

Embodiment C3

(1) Two pipelines with a length of 3 m and a diameter of 0.6 cm are selected as the first pipeline and the second pipeline, and the first pipeline and the second pipeline are connected to both ends of the "Y" type connector (or referred to be as "Y" type connection valve), the other end of the "Y" type connector is connected to the third pipeline, and the third pipeline is a pipeline with a length of 48 m and a diameter of 1.6 cm.

(2) 20,000 kg marigold extract is taken, 80,000 kg anhydrous methanol is added, and the obtained solution is pumped into the first pipeline at a flow rate of 300 mL/min while stirring. 50 kg sodium methoxide is taken to dissolve in 80,000 kg anhydrous methanol and the solution is pumped into the second pipeline at a flow rate of 500 mL/min.

(3) The reaction temperature of the third pipeline is set as 110° C. and the pressure in the third pipeline is set as 1 MPa to perform saponification reaction, and the reaction solution is received at the end of the third pipeline.

Experimental results: the liquid phase composition of the reaction solution is measured, the transesterification rate of the lutein ester in the marigold extract of the reactant reaches 98.15%, the remaining ratio of lutein ester is 0.2%, and the saponification time is 7 min.

Embodiment C4

(1) Two pipelines with a length of 3 m and a diameter of 0.8 cm are selected as the first pipeline and the second pipeline, and the first pipeline and the second pipeline are connected to both ends of the “Y” type connector (or referred to be as “Y” type connection valve), the other end of the “Y” type connector is connected to the third pipeline, and the third pipeline is a pipeline with a length of 96 m and a diameter of 1.6 cm.

(2) 200 kg marigold extract is taken, 800 kg absolute ethanol is added, and the obtained solution is pumped into the first pipeline at a flow rate of 600 mL/min under stirring. 0.2 kg sodium hydroxide is taken to dissolve in 800 kg absolute ethanol and the solution is pumped into the second pipeline at a flow rate of 1000 mL/min.

(3) The reaction temperature of the third pipeline is set as 90° C. and the pressure in the third pipeline is set as 2 MPa to perform saponification reaction, and the reaction solution is received at the end of the third pipeline.

Experimental results: the liquid phase composition of the reaction liquid is measured, the transesterification rate of the lutein ester in the marigold extract of the reactant reaches 99.73%, the remaining ratio of lutein ester is 0.2%, and the saponification time is 7 min.

By comparing embodiments C1-C4, it can be seen that the transesterification rate of lutein ester obtained by tubular reaction for performing saponification reaction is more than 98%, and the saponification time is less than 13 min, indicating that when the tubular reaction is adopted, due to the preheating pipeline (i.e., the first pipeline and the second pipeline) have a certain length (e.g., 2 m) and the preheating pipeline is kept at the preheating temperature (e.g., 85° C.), the reaction raw material may be preheated in advance when passing through the preheating pipeline, which is convenient for subsequent lutein esters to perform rapid saponification under high temperature condition to obtain lutein, and the lutein ester may be converted into lutein with only a small amount of alkali by the alcoholysis method. In the alcoholysis method, lutein ester is decomposed with alcohol to obtain lutein. In this process, anhydrous short-chain alcohol is used as the main reactant for decomposing lutein ester, and alkali is used as a catalyst. That is, the process only needs to use a small amount of alkali, which not only shortens the saponification time, but also reduces labor costs and raw material costs.

Embodiment C5

(1) The reaction solution of embodiment C1 is collected, glacial acetic acid is dropped to the reaction solution, the pH of the reaction solution is adjusted to 8, 0.1 kg tributyl phosphate is added into the reaction solution, the reaction solution is stirred at room temperature, and lutein crystal complex is precipitated.

(2) 0.5% sodium hydroxide solution is prepared, 0.5% sodium hydroxide solution is added to the lutein complex, then filtered after stirring at room temperature for 30 min, the lutein crystal is washed with clean water, and the filter cake is dried at 40° C., the content of lutein crystal in the obtained product is 97.3%, and the yield of lutein crystal reaches 94%.

Embodiment C6

(1) The reaction solution of embodiment C2 is collected, glacial acetic acid is dropped to the reaction solution, the pH of the reaction solution is adjusted to 8, 0.1 kg tributyl phosphate is added to the reaction solution, the reaction solution is stirred at room temperature, and lutein crystal complex is precipitated.

(2) 1% sodium hydroxide solution is prepared, 1% sodium hydroxide solution is added to the lutein complex, then the solution is filtered after stirring at room temperature for 30 min, the lutein crystal is washed with clean water, and the filter cake is dried at 40° C., the content of lutein crystal in the obtained product is 92.3%, and the yield of lutein crystal reaches 88%.

Embodiment C7

(1) The reaction solution of embodiment C3 is collected, hydrochloric acid is dropped to the reaction solution, the pH of the reaction solution is adjusted to 7, 10 kg tributyl phosphate is added, the reaction solution is stirred at room temperature, and lutein crystal complex is precipitated.

(2) 1.3% potassium hydroxide solution is prepared, the 1.3% potassium hydroxide solution is added to the lutein complex, the solution is filtered after stirring at room temperature for 30 min, the lutein crystal is washed with clean water, and the filter cake is dried at 40° C., the content of lutein crystal in the obtained product is 94.67%, and the yield of lutein crystal is 92%.

Embodiment C8

(1) The reaction solution of embodiment C4 is collected, concentrated sulfuric acid is dropped to the reaction solution, the pH of the reaction solution is adjusted to 6, 0.5 kg trioctylamine is added to the reaction solution, the reaction is stirred at room temperature, and lutein crystal complex is precipitate.

(2) 1.8% sodium hydroxide solution is prepared, the 1.8% sodium hydroxide solution is added to the lutein complex, then filtered after stirring at room temperature for 30 min, the lutein crystal is washed with clean water, and the filter cake is dried at 40° C., the content of lutein crystal in the obtained product is 95.57%, and the yield of lutein crystal reaches 90%.

By comparing embodiments C5-C8, it can be seen that lutein crystal may be directly separated by complexing agent, the content of the separated lutein crystal is more than 92%, and the yield of the separated lutein crystal is more than 88%. The method of extracting lutein by complexation does not need to use organic solvent for extraction, so it is environmentally friendly, and can effectively reduce the post-processing process, shorten production time, and improve the production efficiency of lutein crystal.

Comparative Embodiment C1

(1) 200 kg marigold extract is put into the reaction kettle, 4 kg sodium hydroxide and 1200 kg absolute ethanol are added into the reaction kettle, the solution in the reaction kettle is stirred and performed reaction at 60° C. for 3 h, the reaction solution is obtained after the reaction, the liquid phase composition of the reaction solution is measured, the transesterification rate of lutein ester in the reactant marigold extract reaches 99.73%, and the remaining ratio of lutein ester is 0.27%.

(2) The glacial acetic acid is dropped to the obtained reaction solution to adjust the pH of the reaction solution to 8, 0.1 kg tributyl phosphate is added to the reaction solution, the reaction solution is stirred at room temperature and filtered, and the precipitated lutein crystal complex is obtained.

(3) 1.3% potassium hydroxide solution is prepared, 1.3% potassium hydroxide solution is added to the lutein complex, then filter after stirring at room temperature for 30 min, the lutein crystal is washed with clean water, and the filter cake is dried at 40° C., the content of lutein crystal in the obtained product is 93.11%, and the yield of lutein crystal is 88.02%.

TABLE 9

The transesterification rate of lutein ester and the remaining ratio of lutein ester after different reaction time

| Reaction time | Transesterification rate of lutein ester | Remaining ratio of lutein ester after different reaction time |
|---|---|---|
| 1 h | 84.72% | 15.28% |
| 2 h | 90.94% | 9.06% |
| 3 h | 99.73% | 0.27% |

In comparative embodiment C1, as shown in Table 9, the marigold extract is put into the reaction kettle for reaction. After 1 h of reaction, the transesterification rate of lutein ester is 84.72%, and the remaining ratio of lutein ester is 15.28%. After 2 h of reaction, the transesterification rate of lutein ester is 90.94%, and the remaining ratio of lutein ester is 9.06%. When the saponification time is up to 3 h, the transesterification rate of lutein ester reaches 99.73%, and the remaining ratio of lutein ester is 0.27%. Compared with embodiment C4, in the comparative embodiment C1, the transesterification rate of lutein ester reaches 99.73% after 3 h of reaction, while in embodiment C4, when the tubular reaction is used for reaction, the transesterification rate of lutein ester reaches 99.73% when the saponification time is only 7 min, indicating that the tubular reaction using pipelines connected by "Y" type connection valve may quickly react at high temperature to obtain lutein, realizing the continuous reaction of lutein preparation, and greatly reducing the reaction time, at the same time, the tubular reaction reduces manual operation and labor cost.

Comparative Embodiment C2

(1) 200 kg marigold extract is put into the reaction kettle, 50 kg sodium hydroxide and 1200 kg 95% ethanol are added the reaction kettle, the solution in the reaction kettle is stirred and performed reaction at 60° C. for 3 h, the reaction solution is obtained after the reaction, the liquid phase composition of the reaction solution is measured, the transesterification rate of the lutein ester reaches 99.61%, and the remaining ratio of lutein ester is 0.39%.

(2) The glacial acetic acid is dropped to the obtained reaction solution, the pH of the reaction solution is adjusted to 6-7, 1000 kg water is added into the reaction solution, the reaction solution is stirred for 30 min, crude lutein crystal is obtained after filtering, 800 kg 95% ethanol is added into the crude lutein crystal, the temperature of the reaction kettle is kept in a range of 45° C.-50° C. and the reaction solution is stirred for 30 min, and a filter cake is obtained after filtering. The filter cake is dried at 40° C., and the content of the obtained lutein crystal is 88.52%, and the yield of the obtained lutein crystal is 83.74%.

TABLE 10

The transesterification rate of lutein ester and remaining ratio of lutein ester for different reaction time

| Reaction time | Transesterification rate of lutein ester | Remaining ratio of lutein ester |
|---|---|---|
| 1 h | 77.22% | 22.78% |
| 2 h | 94.27% | 5.73% |
| 3 h | 99.61% | 0.39% |

In comparative embodiment C2, as shown in Table 10, the marigold extract is put into the reaction kettle for reaction. After 1 h of reaction, the transesterification rate of lutein ester is 77.22%, and the remaining ratio of lutein ester is 22.78%. After 2 h of reaction, the transesterification rate of lutein ester is 94.27%, and the remaining ratio of lutein ester is 5.73%. When the saponification time is up to 3 h, the transesterification rate of lutein ester reaches 99.61%, and the remaining ratio of lutein ester is 0.39%. Compared with comparative embodiment C1, 50 kg sodium hydroxide is used in comparative embodiment C2, but the transesterification rate of lutein ester is lower than the transesterification rate in comparative embodiment C1 only using 4 kg sodium hydroxide, indicating that the preparation of lutein crystal by alcoholysis (decomposing lutein ester by ethanol) in comparative embodiment C1 can reduce the amount of alkali, and the preparation of lutein crystal by alcoholysis is more complete, which can improve the utilization rate of lutein ester.

Comparing embodiment C4 with comparative embodiment C2, embodiment C4 uses less alkali (in the case of the same reaction of 200 kg marigold extract, embodiment C4 uses 1.2 kg sodium hydroxide and comparative embodiment C2 uses 50 kg sodium hydroxide), saponification time is shorter (saponification time for embodiment C4 is 7 min, and saponification time for comparative embodiment C2 is 3 h), and transesterification rate of lutein ester is higher (the transesterification rate of lutein ester in embodiment C4 is 99.73%, and the transesterification rate of lutein ester in comparative embodiment C2 is 99.61%), indicating that in embodiment C4, the preparation of lutein crystal using tubular reaction combined with alcoholysis method can reduce the use of alkali, which is environmentally friendly, save costs, and significantly shortens the reaction time, thus improving economic benefits.

Compared with embodiments C5-C8, in comparative embodiment C2, lutein is extracted without using a complexing agent, but using 95% ethanol, and the content of lutein crystal in the product is 88.52%, the yield of lutein crystal is 83.74%, which are lower than the content of lutein crystal and yield of lutein crystal of lutein extracted by complexing agent in embodiments C5-C8. This shows that the complexation method may better separate the lutein, which may increase the content and yield of lutein crystal, avoid the use of a large amount of organic solution for extraction, and further reduce the need for solvent washing or crystallization in the later stage and other operations to improve the purity of lutein.

Compared comparative embodiment C 1 and comparative embodiment C2 with embodiments C1-C4, the saponification time of comparative embodiment C1 and comparative embodiment C2 are as long as 3 h, indicating that preparation of lutein using the tubular reaction of embodiments C1-C4 may shorten reaction time of the preparing lutein from lutein ester.

Compared comparative embodiment C2 with embodiments C1-C4, in comparative embodiment C2, 200 kg marigold extract uses 50 kg sodium hydroxide for the reaction, and the transesterification rate of lutein ester after 1 h of reaction is only 77.22%. In embodiment C1, 200 kg marigold extract uses only 0.375 kg sodium ethylate for the reaction, and the transesterification rate of lutein ester is as high as 99.4% after 13 min of reaction. In embodiment C2, 20 kg marigold extract uses only 0.75 kg potassium ethylate for reaction, the transesterification rate of lutein ester is as high as 99.73% after 8 min of reaction. In embodiment C3, 20000 kg marigold extract uses only 50 kg sodium methylate for the reaction, and the transesterification rate of lutein ester is as high as 98.15% after 7 min of reaction. In embodiment C4, 200 kg marigold extract uses only 1.2 kg sodium hydroxide for reaction, and the transesterification rate of lutein ester is as high as 99.73% after 7 min of reaction. This shows that a large amount of sodium hydroxide is used to react in the comparative embodiment C2, and the alcoholysis method is used to prepare lutein crystal in the embodiments C1-C4, which can reduce the amount of alkali when preparing lutein crystal of the same mass, and at the same time, a higher transesterification rate of the lutein ester can be realized within a shorter reaction time, causing that the reaction is more complete and the utilization rate of the lutein ester is improved.

Compared Comparative embodiment C2 with embodiments C5-C8, complexing agent is not used to extract lutein in comparative embodiment C2, content of lutein and yield of lutein are all smaller, indicating the complexing method is used to extract lutein in embodiments C1-C4, which can increase the content lutein crystal and yield of lutein crystal, avoid using a large amount of organic solution for extraction, and further reduce the need for solvent washing or crystallization in the later stage to improve the purity of lutein.

Comparative Embodiment C3

Lutein is prepared according to the method described in Patent Application CN106316909A.

(1) 68.62 kg lutein extract with a lutein content of 16.023% is prepared and is kept at ° C. 37.28 kg potassium hydroxide solution with 35.0% mass concentration is prepared, which is mixed with 82.02 L 95% ethanol solution to form alcohol alkali solution. First, 30.0 kg alcohol-alkali solution and 20.0 kg lutein extract are added into the saponification equipment, the saponification equipment is heated and kept at 60° C., and pre-saponified for 1.5 h to obtain a saponified lutein extract mixture.

(2) The saponification equipment has an effective saponification capacity of 20 kg. The lutein extract and alcohol-alkali solution are added to the saponified lutein extract mixture at a rate of 16.27 kg and 24.41 kg per hour, respectively, and fed continuously for 3 h, the rapid continuous saponification takes 29.5 min, and a lutein saponified solution is obtained.

(3) The lutein saponification solution is diluted with heated water and filtered, and the filter cake is vacuum-dried and weighed by 11.01 kg. The total content of carotenoid is 87.32% and the yield of carotenoid is 87.19% by UV detection.

Compared comparative embodiment C3 with embodiments C1-C8, no tubular reaction and no complexing agent are used in comparative embodiment C3. The preparation process in comparative embodiment C3 has a pre-saponification process before the continuous saponification begins, and the pre-saponification takes 1.5 h, the continuous saponification takes nearly 30 min, and the total time is 2 h, the saponification time is too long, and the pre-saponification process is realized by forced mixing equipment, which is complex and cumbersome to operate.

Comparative Embodiment C4

Lutein is prepared according to the method described in Patent Application CN101260071A.

60 g lutein extract, 120 mL isopropanol, and 60 mL methanol are weighted, the weighted substances are added to the saponification device, 14 g potassium hydroxide and 6 g vitamin C are weighted, the weighted substances are added to the mixing system, the substances are fully stirred and mixed, and saponified at 70° C. for 6 h, nitrogen is introduced into the saponification system, and the substance are distilled under reduced pressure. 250 mL water is added to the obtained concentrate, stirred at room temperature for 40 min, transferred to a separatory funnel, 280 mL dichloromethane is added to extract lutein to form dichloromethane layer and water layer, and the water phase is washed to be colorless and neutral to obtain a dichloromethane layer and water phase without water soluble impurities. Calcium chloride is added to the obtained aqueous phase each time to separate the fatty acid soap, the separated fatty acid calcium soap is combined and filtered, the filter cake is washed with dichloromethane, and the filtrate is incorporated into the dichloromethane layer without water soluble impurity, and then subjected to vacuum distillation to recover the solvent to obtain crude lutein, and 14 g calcium chloride is added. 24 mL mixed solvent consisting of ethyl acetate and petroleum ether is added to the crude lutein, the solution is stirred at room temperature for 30 min and filtered under reduced pressure, and the filter cake is washed with anhydrous methanol until the filtrate is colorless to obtain lutein crystal. The lutein crystal is dried under vacuum at 50° C. for 72 h to obtain 4.0131 g lutein crystal, the content of all trans lutein is 92.71% by high performance liquid chromatography (HPLC).

Compared comparative embodiment C4 with embodiments C1-C8, in comparative embodiment C4, tubular reaction and complexing agent are not used, and saponification time is as long as 6 h in the preparation process, the time is too long, and production capacity is low, moreover, the use of a large amount of potassium hydroxide and the use of dichloromethane as the extraction solvent are not environmentally friendly, and the recovery and treatment of the solvent is cumbersome.

Comparative Embodiment C5

Lutein is prepared according to the method described in Patent Application CN106748947A.

(1) 100 g lutein extract (content of lutein ester is 32%) is dissolved in 250 mL dichloromethane solution at 33° C., the solution is stirred and refluxed for 0.5 h and centrifuged to remove insoluble matter to obtain centrifugal solution.

(2) 250 mL methanol is added to the obtained centrifugal solution, the obtained solution is stirred and refluxed at 33° C. for 0.5 h to form a homogeneous solution, then stood for crystallization at 10° C. for 10 h, and filtered to obtain filter cake I (crude lutein ester), and filtrate is recovered.

(3) The obtained filtrate is transferred into a reaction kettle, the low boiling point solvent dichloromethane is recovered at 40° C., 350 mL n-hexane and 13 g solid sodium hydroxide are added to the remaining solution, nitrogen is filled for protection, and a saponified solution is obtained by saponifying at 50° C. for 2.5 h.

(4) 600 mL deionized water is added to the obtained saponified solution, the obtained solution is stirred and heated at 45° C. for 0.5 h, the pH of the obtained solution is adjusted to 7.4 with acetic acid, and filtered to obtain filter cake II (crude lutein).

(5) The filter cake I (crude lutein ester) and filter cake II (crude lutein) with an aqueous solution of ethanol (isopropanol: water ratio=1:1), and the washed filter cake I and the washed filter cake II are dried under vacuum at 25° C. and −0.095 MPa for 10 h to obtain 24.93 g lutein ester and 2.71 g lutein. The purity of lutein ester is 86.68% and the purity of lutein is 89.01% through UV-visible spectrophotometer detection. The purity of all-trans lutein ester is 91.38% and the purity of all-trans lutein is 92.16% through detection by HPLC. The total utilization rate of raw material is calculated to reach 93.51%.

Compared comparative embodiment C5 with embodiments C1-C8, the preparation process in comparative embodiment C5 uses dichloromethane as the extraction solvent, which is not friendly to the environment, and the saponification time takes 2.5 h, which is long. In addition, the preparation process in comparative embodiment C5 needs to purify the lutein ester in the marigold extract before saponification, and the process is complicated.

The possible beneficial effects of some embodiments of this disclosure include but are not limited to: (1) Carotenoid is pretreated, the mixture of starch and cellulose derivative is used as wall material, and wall material and carbohydrate in a weight ratio of 1:(1-5) are used to prepare pretreated gelling wall material, and carotenoid preparation is prepared based on pretreated carotenoid and pretreated gelling wall materials, which not only can reduce the release rate of carotenoid in hydrochloric acid solution, but also avoid destruction by gastric acid. The carotenoid preparation can maintain the biological activity of carotenoid, effectively reduce the pigment dissolution rate, and avoid dyeing clothes, tongue, hands, etc. in the process of using carotenoid product. (2) Carotenoid is pretreated, starch is used as the wall material, and the wall material and carbohydrate in a weight ratio of (1-5):1 are used to prepare the pretreated gelling wall material, the carotenoid preparation is prepared according to the pretreated carotenoid and gelling wall material, which can not only reduce the release rate of carotenoid in hydrochloric acid solution, avoid destruction by gastric acid, and maintain the biological activity of carotenoid, but also has a large release rate in phosphate buffer, which is conducive to intestinal absorption. The carotenoid preparation can also effectively reduce the pigment dissolution rate and avoid dyeing clothes, tongues, hands, etc. during the use of carotenoid product. (3) Lutein is prepared by tubular reaction combined with alcoholysis, which not only shortens the saponification time, but also converts lutein ester into lutein with only a small amount of alkali, so as to realize environmental protection and reduce labor costs and raw material costs. (4) Lutein is purified by using a complexing agent without requiring the use of organic solvent for extraction, which is environmentally friendly, and can effectively reduce the post-processing process, shorten production time, and improve the production efficiency of lutein crystal. It should be noted that different embodiments may produce different beneficial effects. In different embodiments, the beneficial effects that may be produced may be any one or combination of the above or any other beneficial effects that may be obtained.

It should be noted that the above embodiments are only used to illustrate the technical solution of the disclosure, not to limit the technical solution. Those skilled in the art should understand that those who modify or equivalently replace the technical solution of the disclosure, without departing from the purpose and scope of the technical solution, should be covered in the scope of claims of the disclosure.

Meanwhile, the present disclosure uses specific words to describe the embodiments of the present disclosure. For embodiment, "one embodiment", "an embodiment", and/or "some embodiments" refer to a certain feature, structure or characteristic related to at least one embodiment of this disclosure. Therefore, it is emphasized and should be appreciated that two or more references to "an embodiment" or "one embodiment" or "an alternative embodiment" in various portions of this disclosure are not necessarily all referring to the same embodiment. In addition, certain features, structures or characteristics in one or more embodiments of this disclosure may be properly combined.

What is claimed is:

1. A carotenoid preparation, wherein the carotenoid preparation is obtained by mixing pretreated carotenoid with pretreated gelling wall material, emulsifying a mixture of the pretreated carotenoid and the pretreated gelling wall material, and granulating an emulsified mixture of the pretreated carotenoid and the pretreated gelling wall material; wherein an amount of the pretreated gelling wall material is 40%-80% of a weight of the carotenoid preparation; and raw material of the pretreated gelling wall material includes wall material and carbohydrate; wherein the wall material includes modified starch or a mixture of starch and cellulose derivative;

the carbohydrate includes at least one of sucrose, glucose, glucose syrup, xylose, maltooligosaccharide, fructooligosaccharide, and solid corn syrup;

the pretreated carotenoid is obtained by mixing and stirring carotenoid and ethanol solution, pretreating a mixture of the carotenoid and the ethanol solution by high-speed shear dispersion, and solvent removal; and the pretreated gelling wall material is obtained by mixing the wall material and the carbohydrate.

2. The carotenoid preparation of claim 1, wherein the carotenoid includes at least one of lutein, lutein fatty acid ester, zeaxanthin, lycopene, α-carotene, β-carotene, canthaxanthin, and astaxanthin.

3. The carotenoid preparation of claim 1, wherein raw material of the pretreated carotenoid is obtained by mixing lutein or lutein fatty acid ester, zeaxanthin, and β-carotene in a weight ratio of (1-3):(1-3):(1-3).

4. The carotenoid preparation of claim 1, wherein a pigment content of the pretreated carotenoid is greater than 70%.

5. The carotenoid preparation of claim 1, wherein the starch and the cellulose derivative are mixed in a weight ratio of 1:(1-2).

6. The carotenoid preparation of claim 1, wherein the modified starch is starch sodium octenyl succinate.

7. The carotenoid preparation of claim 1, wherein the wall material and the carbohydrate are mixed in a weight ratio of 1:(1-5).

8. The carotenoid preparation of claim 1, wherein the wall material and the carbohydrate are mixed in a weight ratio of (1-5):1.

9. The carotenoid preparation of claim 1, wherein a pigment dissolution rate of the carotenoid preparation in water is less than 1%.

10. The carotenoid preparation of claim 1, wherein a pigment dissolution rate of the carotenoid preparation in water is less than 5%, and a release rate of the carotenoid preparation in gastrointestinal fluid for 0.5 h is less than 35%, and the release rate of the carotenoid preparation in the gastrointestinal fluid for 4 h is greater than 90%.

11. The carotenoid preparation of claim 1, wherein a moisture content of the pretreated carotenoid is within a range of 10%-30%.

* * * * *